US010555961B2

(12) United States Patent
Molitoris et al.

(10) Patent No.: US 10,555,961 B2
(45) Date of Patent: Feb. 11, 2020

(54) MATERIALS AND METHODS FOR TREATING BACTERIAL INFECTIONS USING C-1 GENTAMICIN

(71) Applicants: INDIANA UNIVERSITY RESEARCH AND TECHNOLOGY CORPORATION, Indianapolis, IN (US); United States Government as represented by the Department of Veterans Affairs, Washington, DC (US)

(72) Inventors: Bruce A. Molitoris, Indianapolis, IN (US); Mark C. Wagner, Indianapolis, IN (US); Ruben M. Sandoval, Indianapolis, IN (US); Mark Gerard Goebl, Indianapolis, IN (US)

(73) Assignees: INDIANA UNIVERSITY RESEARCH AND TECHNOLOGY CORPORATION, Indianapolis, IN (US); UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 15/579,487

(22) PCT Filed: Jun. 3, 2016

(86) PCT No.: PCT/US2016/035768
§ 371 (c)(1),
(2) Date: Dec. 4, 2017

(87) PCT Pub. No.: WO2016/196964
PCT Pub. Date: Dec. 8, 2016

(65) Prior Publication Data
US 2018/0147229 A1 May 31, 2018

Related U.S. Application Data

(60) Provisional application No. 62/171,762, filed on Jun. 5, 2015.

(51) Int. Cl.
*A61K 31/7036* (2006.01)
*A61P 35/00* (2006.01)
*A61K 31/351* (2006.01)

(52) U.S. Cl.
CPC ........ *A61K 31/7036* (2013.01); *A61K 31/351* (2013.01); *A61P 35/00* (2018.01)

(58) Field of Classification Search
None
See application file for complete search history.

(56) References Cited

U.S. PATENT DOCUMENTS

| 3,091,572 A | 5/1963 | Luedemann et al. | |
|---|---|---|---|
| 3,136,704 A | 6/1964 | Charney | |
| 3,651,042 A * | 3/1972 | Marquez | C07H 15/236 536/13.6 |
| 3,780,018 A * | 12/1973 | Konishi | C07H 15/236 536/13.6 |
| 8,951,978 B2 | 2/2015 | Molitoris et al. | |

FOREIGN PATENT DOCUMENTS

| CN | 1557958 A | 12/2004 |
|---|---|---|
| WO | WO 2004/105688 A2 | 12/2004 |
| WO | WO 2008/067491 A2 | 6/2008 |

OTHER PUBLICATIONS

European Patent Application No. 16 80 4542 Supplementary European Search Report dated Jan. 8, 2019.
Kase et al., 'Sagamicin and the related aminoglycosides: fermentation and biosynthesis. I, Biosynthetic studies with the blocked mutants of Micromonospore sagamiensis.', J Antibiot (Tokyo). Jan. 1982;35(1):1-9., [online] [retrieved on Jan. 8, 2019]. Retrieved from the Internet: < URL: https://www.ncbi.nlm.nih.gov/pubmed/7082452>.
Kohlhepp et al., 'Nephrotoxicity of the constituents of the gentamicin complex.', J Infect Dis. Apr. 1984;149(4):605-14., [online] [retrieved on Jan. 8, 2019]. Retrieved from the Internet: < URL: https://www.ncbi.nlm.nih.gov/pubmed/6725992>.
White et al., 'Variations in gentamicin C1, C1a, C2, and C2a content of some preparations of gentamicin sulphate used clinically as determined by high-performance liquid chromatography.', Ther Drug Monit. 1983;5(1):123-6. [online] [retrieved on Jan. 8, 2019]. Retrieved from the Internet: < URL: https://www.ncbi.nlm.nih.gov/pubmed/6845395>.
Belais et al., "In vitro readthrough of termination codons by gentamycin in the Stüve-Wiedemann Syndrome," *Eur. J. Hum. Genet.* 18(1): 130-132 (2010).
Bidou et al., "Premature stop codons involved in muscular dystrophies show a broad spectrum of readthrough efficiencies in response to gentamicin treatment," *Gene Therapy* 11: 619-627 (2004).
Bykov et al., "Mutant p53 reactivation by small molecules makes its way to the clinic," *FEBS Lett.* 588: 2622-2627 (2014).
Corridon et al., "A method to facilitate and monitor expression of exogenous genes in the rat kidney using plasmid and viral vectors," *Am. J. Physiol. Renal Physiol.* 304(9): F1217-F1229 (2013).
Dickson et al., "The proximal tubule and albuminuria: really!," *J. Am. Soc. Nephrol.* 25(3): 443-453 (2014).
Floquet et al., "Rescue of non-sense mutated p53 tumor suppressor gene by aminoglycosides," *Nucleic Acids Res* 39(8): 3350-62 (2011).
Keeling et al., "Pharmacological suppression of premature stop mutations that cause genetic diseases," *Current Pharmacogenomics* 3(4): 259-269 (2005).

(Continued)

*Primary Examiner* — Dale R Miller
(74) *Attorney, Agent, or Firm* — Woodard, Emhardt, Henry, Reeves & Wagner, LLP

(57) ABSTRACT

Various aspects relate to the use of C-1 gentamicin as an antibiotic effective for the treatment of a bacterial infection, a genetic disorder, or cancer in a subject.

17 Claims, 7 Drawing Sheets

Specification includes a Sequence Listing.

(56) References Cited

OTHER PUBLICATIONS

Mosegaard et al., "Gentamicin and gentamicin C1 in the treatment of complicated urinary tract infections: comparative study of efficacy, tolerance, and pharmacokinetics," *Antimicrobial Agents and Chemotherapy* 7(3): 328-332 (1975).
Sandoval et al., "A Non-Nephrotoxic Gentamicin Congener That Retains Antimicrobial Efficacy," *J. Am. Soc. Nephrol.* 17(10): 2697-2705 (2006).
Tao et al. "A practical method for monitoring FRET-based biosensors in living animals using two-photon microscopy," *Am. J. Physiol. Cell Physiol.* 309(11): C724-735 (2015).
Zeitlin, "Novel pharmacologic therapies for cystic fibrosis," *J. Clin. Invest.* 103: 447-452 (1999).
Zilberberg et al., "Restoration of APC gene function in colorectal cancer cells by aminoglycoside- and macrolide-induced read-through of premature termination codons," *Gut* 59(4): 496-507 (2010).
Israel Patent Office, International Search Report in International Application PCT/US2016/035768 (dated Sep. 22, 2016).
Israel Patent Office, Written Opinion in International Application PCT/US2016/035768 (dated Sep. 22, 2016).
International Bureau of WIPO, International Preliminary Report on Patentability in International Application PCT/US2016/035768 (dated Dec. 14, 2017).

\* cited by examiner

SEQUENCE LISTING

<160> NUMBER OF SEQ ID NOS: 12

<210> SEQ ID NO 1
<211> LENGTH: 27
<212> TYPE: DNA
<213> ORGANISM: Artificial Sequence
<220> FEATURE:
<223> OTHER INFORMATION: Synthetic sequence

<400> SEQUENCE: 1
gatcacatgt gctaacaggt ctatgcc        27

<210> SEQ ID NO 2
<211> LENGTH: 27
<212> TYPE: DNA
<213> ORGANISM: Artificial Sequence
<220> FEATURE:
<223> OTHER INFORMATION: Synthetic sequence

<400> SEQUENCE: 2
caggatttgg aatagaggcg tcccagt        27

<210> SEQ ID NO 3
<211> LENGTH: 27
<212> TYPE: DNA
<213> ORGANISM: Artificial Sequence
<220> FEATURE:
<223> OTHER INFORMATION: Synthetic sequence

<400> SEQUENCE: 3
agcccatttc cttgacagca tttggaa        27

<210> SEQ ID NO 4
<211> LENGTH: 27
<212> TYPE: DNA
<213> ORGANISM: Artificial Sequence
<220> FEATURE:
<223> OTHER INFORMATION: Synthetic sequence

<400> SEQUENCE: 4
ttgaaagagc aataaaatgg cttcaac        27

<210> SEQ ID NO 5
<211> LENGTH: 27
<212> TYPE: DNA
<213> ORGANISM: Artificial Sequence
<220> FEATURE:
<223> OTHER INFORMATION: Synthetic sequence

<400> SEQUENCE: 5
cacaaagcag agatatgact tgataag        27

<210> SEQ ID NO 6
<211> LENGTH: 30
<212> TYPE: DNA
<213> ORGANISM: Artificial Sequence
<220> FEATURE:
<223> OTHER INFORMATION: Synthetic sequence

<400> SEQUENCE: 6
agttaccacc tggtcttgtg agcctataca        30

<210> SEQ ID NO 7
<211> LENGTH: 30
<212> TYPE: DNA
<213> ORGANISM: Artificial Sequence
<220> FEATURE:
<223> OTHER INFORMATION: Synthetic sequence

<400> SEQUENCE: 7
gctcaaacca agtgagaagt acctaaaaat                                30

<210> SEQ ID NO 8
<211> LENGTH: 24
<212> TYPE: DNA
<213> ORGANISM: Artificial Sequence
<220> FEATURE:
<223> OTHER INFORMATION: Synthetic sequence

<400> SEQUENCE: 8
ctggcccctc cttagcatct tatc                                      24

<210> SEQ ID NO 9
<211> LENGTH: 24
<212> TYPE: DNA
<213> ORGANISM: Artificial Sequence
<220> FEATURE:
<223> OTHER INFORMATION: Synthetic sequence

<400> SEQUENCE: 9
agaaacactt tttgacatag tgtg                                      24

<210> SEQ ID NO 10
<211> LENGTH: 27
<212> TYPE: DNA
<213> ORGANISM: Artificial Sequence
<220> FEATURE:
<223> OTHER INFORMATION: Synthetic sequence

<400> SEQUENCE: 10
aatatagttc ttggagaagg tggaatc                                   27

<210> SEQ ID NO 11
<211> LENGTH: 60
<212> TYPE: DNA
<213> ORGANISM: Artificial Sequence
<220> FEATURE:
<223> OTHER INFORMATION: Synthetic Sequence

<400> SEQUENCE: 11
gacgagctgt acaagtccgg actcagatcc ccaccggtcg ccaccatggt gagcaagggc    60

<210> SEQ ID NO 12
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 12

Asp Glu Leu Tyr Lys Ser Gly Leu Arg Ser Pro Pro Val Ala Thr Met
1               5                   10                  15

Val Ser Lys Gly
            20

MATERIALS AND METHODS FOR TREATING BACTERIAL INFECTIONS USING C-1 GENTAMICIN

CROSS-REFERENCE TO RELATED APPLICATIONS

This patent application is a U.S. national phase of International Patent Application No. PCT/US2016/035768, filed Jun. 3, 2016, which claims the benefit of U.S. Provisional Patent Application No. 62/171,762, filed Jun. 5, 2015, the disclosures of which are incorporated by reference for all purposes.

STATEMENT OF GOVERNMENTAL RIGHTS

This invention was made with government support under DK061594 awarded by the National Institutes of Health and BX001137 merit award by the Veterans Administration. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,734 Byte ASCII (Text) file named "736354_ST25.TXT," created on Nov. 30, 2017.

BACKGROUND

Many aminoglycosides exhibit antibacterial activity and have been used to treat certain bacterial infections. Some of these compounds, including native gentamicin, have been found to be especially useful in the treatment of infections caused by gram-negative bacteria including pathogenic species of *Pseudomonas*, and mycobacteria. However, the widespread use of aminoglycosides as antibiotics for the treatment of humans and animals has been limited due to the lack of availability of safer and more effective forms.

BRIEF SUMMARY OF THE INVENTION

Aspects of the present invention include the use of the C-1 congener of gentamicin as an antibiotic. Some aspects of the invention include formulating a composition comprising C-1 gentamicin or a pharmaceutically acceptable acid addition salt thereof, a preservative, and a chelating agent, wherein the composition is a liquid, and the composition is substantially free of C-1a gentamicin or C-2a gentamicin or substantially free of both C-1a gentamicin and C-2a gentamicin. It was discovered that such composition exhibits lower nephrotoxicity than a correspondingly effective antibiotic formulation that includes native gentamicin. The composition optionally comprises at least one additional antibiotic.

Still other aspects provide a course of treatment comprising administering to a human or an animal subject at least one therapeutically effective course of treatment with the C-1 congener of gentamicin or a pharmaceutically acceptable acid addition salt thereof to treat a bacterial infection, a genetic disease, or cancer. In some embodiments, the therapeutically effective course of treatment includes administering at least one additional antibiotic. In some embodiments, the at least one antibiotic is administered before the patient is treated with a therapeutically effective amount of the C-1 congener of gentamicin. In still other embodiments, the patient can be treated with a least one therapeutically effective dose of the C-1 congener of gentamicin before the patient is treated with the first dose of another antibiotic.

The C-1 congener of gentamicin ("C-1 gentamicin") is the molecule depicted by Formula (I), wherein $R^1=R^2=CH_3$, and $R^3=H$.

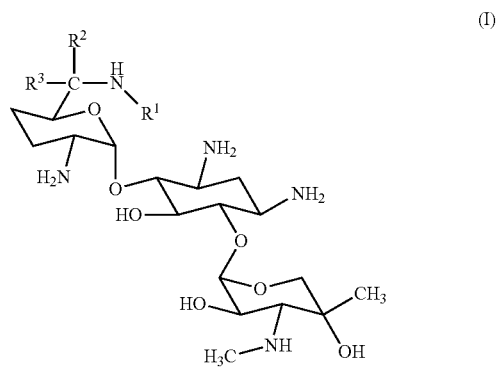

(I)

In certain embodiments, the compound C-1 gentamicin exhibits both lower nephrotoxicity than native gentamicin and good antibiotic activity.

DETAILED DESCRIPTION OF THE INVENTION

Figure 1:
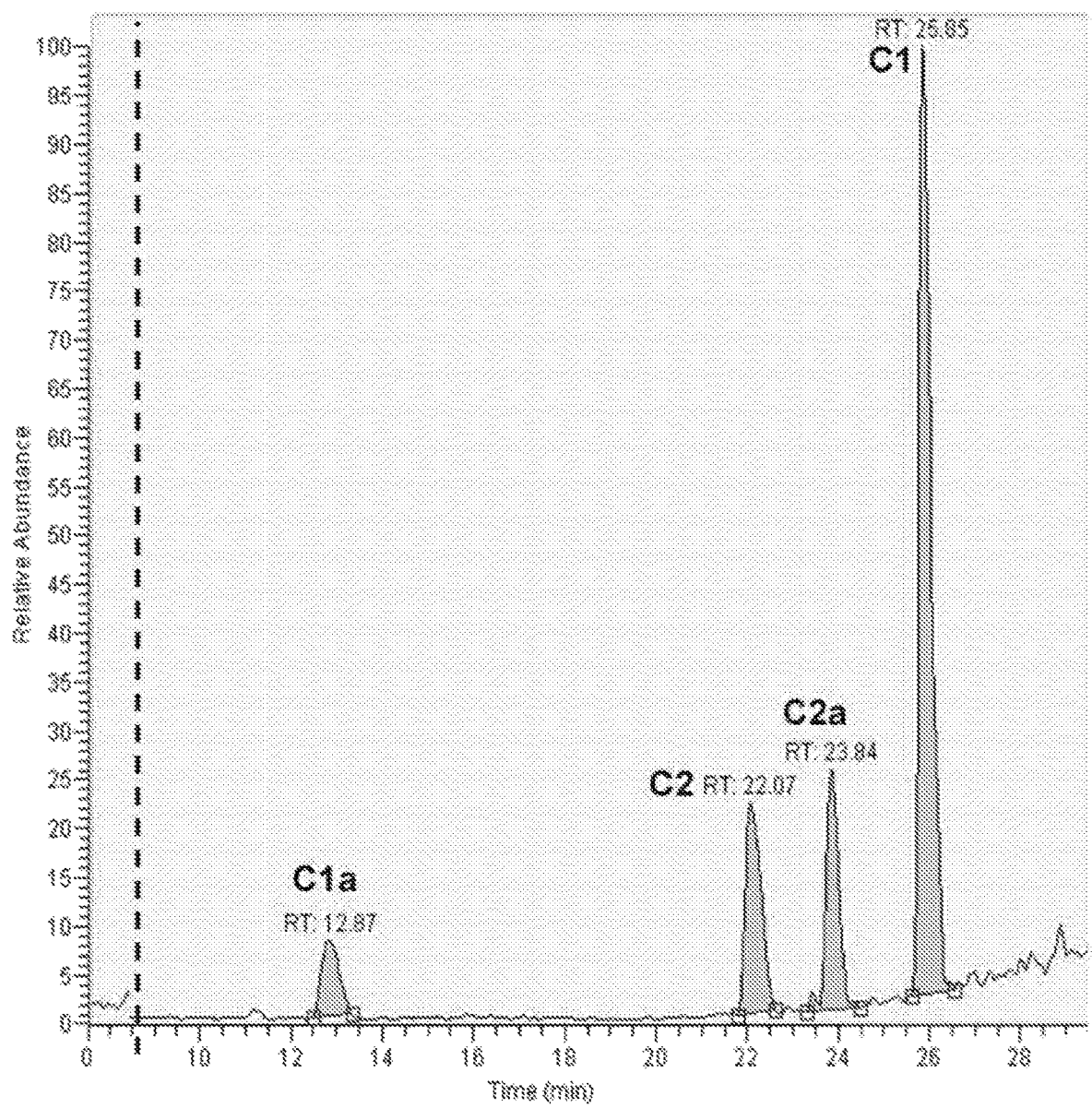
FIG. 1 is an HPLC trace illustrating the separation of individual congeners of gentamicin, including the enantiomers C-1, C-1a, C-2 and C-2a, with no apparent cross-contamination.

Gentamicin is a complex produced by fermentation of *Micromonospora purpurea* or *Micromonospora echinospora* and variants thereof as described, for example, by U.S. Pat. Nos. 3,091,572 and 3,136,704, each of which is incorporated herein by reference in its entirety.

Analysis has shown that the gentamicin complex is composed of at least four closely related, isomeric pseudo-oligosaccharides, each having a characteristic structure in which 2-deoxystreptamine is linked to two saccharide units, namely, garosamine and purpurosamine (see U.S. Pat. No. 8,951,978 and International Publication No. WO 2004/105688 A2, hereby incorporated by reference). These four major gentamicin components differ from one another only in the nature of the methylation of the amine group at the 6' carbon of the purpurosamine unit linked to the 2-deoxystreptamine at the C-4 position, as can be seen in the structure of Formula (I):

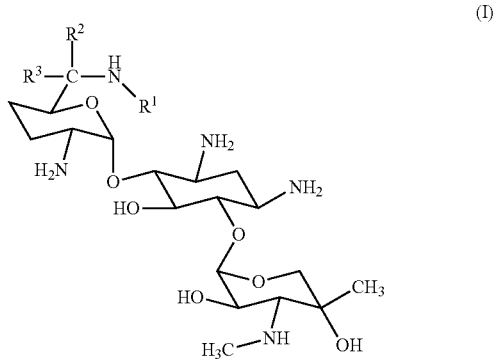

Gentamicin: C-1: $R_1=R_2=CH_3$; $R_3=H$
C-1a: $R_1=R_2=R_3=H$
C-2: $R_1=R_3=H$; $R_2=CH_3$
C-2a: $R_1=R_2=H$; $R_3=CH_3$ Clinically significant nephrotoxicity is characterized by elevated serum creatinine levels and a reduced Glomerular Filtration Rate (GFR). Accordingly, it is relatively easy to assess the damage done to the renal system by various nephrotoxins including, for example, many aminoglycosides. Numerous strategies have been developed to minimize the nephrotoxicity that is associated with aminoglycoside antibiotics. Approaches to limiting the toxicity of these compounds have included the introduction of an agent that alters uptake of the drugs or the intracellular trafficking of aminoglycosides. In this regard, high levels of dietary calcium or the use of polyaspartic acid has shown beneficial effects in animal models for nephrotoxicity. Another approach has been purification of nontoxic native components from mixtures of aminoglycosides or the chemical modification of toxic aminoglycosides to produce less toxic substances. This approach has yielded two commercially available aminoglycosides that exhibit somewhat less nephrotoxicity than many commonly used aminoglycosides. Although certain aminoglycoside antibiotics are less nephrotoxic than others, most still exhibit an unacceptably high level of nephrotoxicity, and these compounds are especially ill-suited for treating patients at high-risk for kidney problems.

Early clinical observations indicated that the nephrotoxicity of different gentamicin manufacturing lots were different. This led Kohlepp et al. to initiate studies to try and determine the relative toxicity of the various gentamicin components in animals (see, e.g., Kohlepp et al., *J. Infect. Dis.*, 149: 605-614 (1984)). Kohlepp et al. failed to cleanly separate gentamicin into its various components, however, and thus, their studies were performed with mixtures of gentamicin congeners, which may have been enriched in a given congener of gentamicin, such as C-1, C-1a, or C-2. Isolated or purified congeners of gentamicin were not obtained or tested. Additionally, a new congener of gentamicin C-2a is disclosed herein, which was not identified by Kohlepp et al. and may have contaminated their partially purified fractions.

Methods that may be used to purify and isolate components of gentamicin are disclosed, for example, in Sandoval et al. (*J. Am. Soc. Nephrol.*, 17: 2697-2705 (2006)), as well as U.S. Pat. No. 8,951,978, hereby incorporated by reference.

In some aspects, the invention relates to the findings that the C-1 congener of gentamicin ("C-1 gentamicin") is both non-nephrotoxic and a potent bactericide against gram-positive and multi-drug-resistant gram-negative bacteria. Given its good antibacterial activity and low cytotoxicity, the C-1 congener is useful in the treatment of infectious diseases.

Many aminoglycoside antibiotics are associated with a high incidence of acute renal failure (ARF). More aggressive and broader therapeutic regimens using this less toxic compound can be used with patients who previously were deemed unsuitable for treatment with gentamicin because of their kidney disease or preexisting risk factors for developing kidney disease. Moreover, understanding the mechanisms of gentamicin's renal toxicity may provide insights leading to the development of co-therapies that use gentamicin.

In some aspects, the invention relates to compositions comprising C-1 gentamicin. In preferred embodiments, the composition is substantially free of C-1a gentamicin, C-2a gentamicin, or C-2 gentamicin, or substantially free of two or all three of these compounds. In preferred embodiments, the composition is substantially free of both C-1a gentamicin and C-2a gentamicin. In some embodiments, the composition comprises C-2 gentamicin. The composition can comprise a salt of gentamicin, such as gentamicin sulfate, e.g., the composition comprises C-1 gentamicin sulfate.

In preferred embodiments, the composition has a ratio of C-1a gentamicin to C-1 gentamicin of less than 1:10 (w/w), such as less than 1:20 (w/w), less than 1:50 (w/w), less than 1:100 (w/w), or even less than 1:1000 (w/w). In preferred embodiments, the composition has a ratio of C-2a gentamicin to C-1 gentamicin of less than 1:10 (w/w), such as less than 1:20 (w/w), less than 1:50 (w/w), less than 1:100 (w/w), or even less than 1:1000 (w/w).

In some embodiments, the composition has a ratio of C-2 gentamicin to C-1 gentamicin of less than 1:10 (w/w), such as less than 1:20 (w/w), less than 1:50 (w/w), less than 1:100 (w/w), or even less than 1:1000 (w/w).

In preferred embodiments, the composition has a ratio of C-1a gentamicin to total gentamicin (i.e., C1, C-1a, C-2, and C-2a gentamicin) of less than 1:10 (w/w), such as less than 1:20 (w/w), less than 1:50 (w/w), less than 1:100 (w/w), or even less than 1:1000 (w/w). In preferred embodiments, the composition has a ratio of C-2a gentamicin to total gentamicin of less than 1:10 (w/w), such as less than 1:20 (w/w), less than 1:50 (w/w), less than 1:100 (w/w), or even less than 1:1000 (w/w).

In some embodiments, the composition has a ratio of C-2 gentamicin to total gentamicin (i.e., C1, C-1a, C-2, and C-2a gentamicin) of less than 1:10 (w/w), such as less than 1:20 (w/w), less than 1:50 (w/w), less than 1:100 (w/w), or even less than 1:1000 (w/w).

In preferred embodiments, the composition has a ratio of C-1 gentamicin to total gentamicin (i.e., C-1, C-1a, C-2, and C-2a gentamicin) of greater than 9:10 (w/w), such as greater than greater than 19:20 (w/w), greater than 49:50 (w/w), greater than 99:100 (w/w), greater than 199:200 (w/w), or even greater than 499:500 (w/w).

In any of the embodiments set forth herein, the composition is a liquid. For example, in some embodiments, the composition is a liquid, and the composition comprises C-1 gentamicin at a concentration between about 0.1 mg/mL and about 115 mg/mL, such as between about 0.3 mg/mL and about 30 mg/mL or between about 10 mg/mL and about 100 mg/mL. The composition can comprise C-1 gentamicin at a concentration of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, or about 50 mg/mL.

In some embodiments, the composition is a liquid, and the composition comprises C-2 gentamicin at a concentration between about 0.1 mg/mL and about 115 mg/mL, such as between about 0.3 mg/mL and about 30 mg/mL or between about 10 mg/mL and about 100 mg/mL. The composition may comprise C-2 gentamicin at a concentration of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, or about 50 mg/mL.

In some embodiments, the composition is a liquid and the composition comprises total gentamicin (i.e., C-1, C-1a, C-2, and C-2a gentamicin) at a concentration between about 0.1 mg/mL and about 115 mg/mL, such as between about 0.3 mg/mL and about 30 mg/mL or between about 10 mg/mL and about 100 mg/mL. The composition can comprise a total gentamicin at a concentration of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, or about 50 mg/mL.

In some preferred embodiments, the composition comprises less than 1000 ppm C-1a gentamicin, such as less than 900 ppm, less than 800 ppm, less than 700 ppm, less than 600 ppm, less than 500 ppm, less than 400 ppm, less than 300 ppm, less than 200 ppm, less than 100 ppm, less than 90 ppm, less than 80 ppm, less than 70 ppm, less than 60 ppm, less than 50 ppm, less than 40 ppm, less than 30 ppm, less than 20 ppm, or even less than 10 ppm C-1a gentamicin.

In some preferred embodiments, the composition comprises less than 1000 ppm C-2a gentamicin, such as less than 900 ppm, less than 800 ppm, less than 700 ppm, less than 600 ppm, less than 500 ppm, less than 400 ppm, less than 300 ppm, less than 200 ppm, less than 100 ppm, less than 90 ppm, less than 80 ppm, less than 70 ppm, less than 60 ppm, less than 50 ppm, less than 40 ppm, less than 30 ppm, less than 20 ppm, or even less than 10 ppm C-2a gentamicin.

In some embodiments, the composition comprises less than 1000 ppm C-2 gentamicin, such as less than 900 ppm, less than 800 ppm, less than 700 ppm, less than 600 ppm, less than 500 ppm, less than 400 ppm, less than 300 ppm, less than 200 ppm, less than 100 ppm, less than 90 ppm, less than 80 ppm, less than 70 ppm, less than 60 ppm, less than 50 ppm, less than 40 ppm, less than 30 ppm, less than 20 ppm, or even less than 10 ppm C-2 gentamicin.

The composition can further comprise at least one additional antibiotic that is not a congener of gentamicin. The at least one additional antibiotic can be any suitable antibiotic (e.g., an aminoglycoside antibiotic) that kills or inhibits the growth of gram positive and/or gram negative bacteria. Typical antibiotics include, for example, streptomycin, kanamycin, spectinomycin, neomycin (e.g., neomycin B, neomycin C, or neomycin E), and amikacin, dibekacin, sisomicin, netilmicin, tobramycin, prontosil, geldanamycin, herbimycin, rifaximin, ertapnenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditroen, cefoperazone, cefotaxime, cefpodoxime, cefitizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicilin, azlocillin, carbenicillin, cloxacillin, dicloxacillan, flucloxacillin, mezlocillin, methicillin, nafcillin, oxacillin, penicillin (e.g., penicillin G, or penicillin V), piperacillin, temocillin, ticarcillin, clavulanate, sulbactam, tazobactam, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfasalazine, sulfisoxazole, co-timoxazole, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, arsphenamine, chloramphenicol, fosfomycin, fusidic acid, metronidazole, mupirocin, platesimycin, quinupristin, dalfopristin, thiamphenicol, tigecycline, tinidazole, trimethoprim, and any combination thereof.

The composition can further comprise at least one preservative and/or chelating agent. Suitable preservatives include an antioxidant (e.g., ascorbic acid, citric acid) or benzalkonium chloride, benzoic acid, sorbic acid, chlorhexidene, phenol, 3-cresol, benzyl alcohol, phenethyl alcohol, salicylic acid, thimerosal, hydrogen peroxide, sodium benzoate, methyl-, ethyl-, or propyl-hydroxybenzoate (i.e., the parabens), and mixtures thereof. Suitable chelating agents include ethylenediamine, ethylenediamine tetraacetic acid (EDTA), diethylene triamine pentaacetic acid (DTPA), N-{2 [bis(carboxymethyl)amino]ethyl}-N-(2-hydroxyethyl)glycine (HEDTA), porphin, dihydroxyethyl glycine, tartaric acid, and mixtures thereof.

In certain embodiments, the invention provides a composition comprising C-1 gentamicin or a pharmaceutically acceptable acid addition salt thereof, optionally at least one additional antibiotic that is not gentamicin, a preservative, and a chelating agent, wherein the composition is a liquid, and the composition is substantially free of C-1a gentamicin or C-2a gentamicin or substantially free of both C-1a gentamicin and C-2a gentamicin.

While not wishing to be bound by any theory, it is believed that gentamicin can induce suppression of premature termination codons (PTC), and as such, can provide therapeutic treatment for cancer and genetic diseases, such as monogenic diseases. The phrase "suppression of a premature termination codon" refers to the translation of open reading frames both upstream and downstream of the premature termination codon into a single polypeptide. Accordingly, in some aspects, the invention is directed to a method of suppressing PTC in a cell or subject. The cell can be from any suitable tissue or organ, as such blood, muscle, a nerve, spinal cord, epithelial tissue, skin, brain, heart, lungs, stomach, reproductive system, thyroid, liver, kidney, prostate, eye, pancreas, spleen, bladder, bone, a gland (e.g., adrenal gland, salivary gland, pituitary gland, thymus gland, parathyroid gland), ureter, trachea, gall bladder, intestine, urethra, or lymph node.

The invention further provides methods of using a composition comprising C-1 gentamicin, as described herein, to treat a particular disorder in a subject.

In some aspects the invention relates to a method for preventing or treating a bacterial infection in a subject, comprising administering to the subject a composition comprising a therapeutically effective amount of C-1 gentamicin or a pharmaceutically acceptable acid addition salt thereof as described herein. The bacterial infection can be caused by a gram positive or gram negative bacteria (e.g., *Bacillus, Klebsiella, Streptococcus, Staphylococcus, E. coli, Listeria, Brucella, Bartonella henselae, Erysipeloid rhusiopathiae, Neisseria gonorrhoeae, Neisseria meningitidis, Borrelia, Salmonella, Vibrio cholerae, Pseudomonas, Francisella tularensis, Shigella*, and *Leptospira*). In some embodiments, the bacterial infection is cholera, anthrax, listeriosis, lyme disease, shigellosis, tularemia, tetanus, toxic shock syndrome, leptospirosis, a *Pneumococcal* infection, a *Salmonella* infection, a *Staphylococcus aureus* infection, a *Pseudomonas* infection, a *Streptococcal* infection, a *Meningococcal* infection, a *Bacillus subtilis* infection, a *Klebsiella pneumonia* infection, or an *E. coli* infection. In certain embodiments, the bacterial infection is a *Bacillus subtilis* or *Klebsiella pneumonia* infection, such as a multi-drug resistant *Klebsiella pneumonia* infection.

The method can further comprise administering at least one additional antibiotic to the subject. The antibiotic can be any suitable antibiotic (e.g., an aminoglycoside antibiotic) that kills or inhibits the growth of gram positive and/or gram negative bacteria. Typical antibiotics include, for example, streptomycin, kanamycin, spectinomycin, neomycin (e.g., neomycin B, neomycin C, or neomycin E), and amikacin, dibekacin, sisomicin, netilmicin, tobramycin, prontosil, geldanamycin, herbimycin, rifaximin, ertapnenem, doripenem, imipenem, cilastatin, meropenem, cefadroxil, cefazolin, cefalotin, cefalexin, cefaclor, cefamandole, cefoxitin, cefprozil, cefuroxime, cefixime, cefdinir, cefditroen, cefoperazone, cefotaxime, cefpodoxime, cefitizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicilin, azlocillin, carbenicillin, cloxacillin, dicloxacillan, flucloxacillin, mezlocillin, methicillin, nafcillin, oxacillin, penicillin (e.g., penicillin G, or penicillin V), piperacillin, temocillin, ticarcillin, clavulanate, sulbactam, tazobactam, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfasalazine, sulfisoxazole, co-timoxazole, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, arsphenamine, chloramphenicol, fosfomycin, fusidic acid, metronidazole, mupirocin, platesimycin, quinupristin, dalfopristin, thiamphenicol, tigecycline, tinidazole, trimethoprim, and combinations thereof. In some embodiments, the at least one antibiotic (e.g., aminoglycoside antibiotic) is administered before the patient is treated with a therapeutically effective amount of the C-1 congener of gentamicin. In still other embodiments, the patient can be treated with a least one therapeutically effective dose of the C-1 congener of gentamicin or a pharmaceutically acceptable acid addition salt thereof before the patient is treated with the first dose of another antibiotic (e.g., aminoglycoside antibiotic).

The invention further relates to a method for treating a genetic disease in a subject, comprising administering to the subject a composition comprising a therapeutically effective amount of C-1 gentamicin or a pharmaceutically acceptable acid addition salt thereof as described herein. In preferred embodiments, the genetic disease is caused by a premature stop codon in a gene (i.e., in the open reading frame of a gene). The premature stop codon may, for example, decrease the amount of functional protein in the subject or increase the amount of a deleterious, truncated protein in the subject. The premature stop codon can be UAAC, UAGC, UGAC, UAAG, UAGG, UGAG, UAAU, UAGU, UGAU, UAAA, UAGA, or UGAA. In some embodiments, the premature stop codon is UAA, UGA, or UAG. The genetic disease can be, for example, cystic fibrosis, Hurler Syndrome, Scheie syndrome, Duchenne muscular dystrophy, Becker muscular dystrophy, nephrogenic diabetes insipidus, hemophilia (e.g., hemophilia A, hemophilia B, or hemophilia C, particularly hemophilia A), adenomatous polyposis coli (APC)-mediated colon cancer, dystrophic epidermolysis bullosa (DEB), or Kabuki syndrome (KS). Methods for treating genetic diseases in a subject comprising the administration of gentamicin are described in U.S. Pat. No. 8,951,978, hereby incorporated by reference.

In some aspects, the invention relates to a method for treating cancer in a subject, comprising administering to the subject a composition comprising a therapeutically effective amount of C-1 gentamicin or a pharmaceutically acceptable acid addition salt thereof as described herein, wherein the cancer cells comprise a premature stop codon in the open reading frame of a gene. For example, the cancer can comprise a premature stop codon in a gene encoding p53. The premature stop codon can be UAAC, UAGC, UGAC, UAAG, UAGG, UGAG, UAAU, UAGU, UGAU, UAAA, UAGA, or UGAA. In some embodiments, the premature stop codon is UAA, UGA, or UAG. Methods for treating cancer in a subject comprising the administration of gentamicin are described in U.S. Pat. No. 8,951,978, hereby incorporated by reference.

Non-limiting examples of specific types of cancers include cancer of the head and neck, eye, skin, mouth, throat, esophagus, chest, bone, lung, colon, sigmoid, rectum, stomach, prostate, breast, ovaries, kidney, liver, pancreas, brain, intestine, heart or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelioma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocyctic leukemia, acute undifferentiated leukemia, chronic myelocytic leukemia, chronic lymphocytic leukemia, hairy cell leukemia, or multiple myeloma. See, e.g., *Harrison's Principles of Internal Medicine*, Eugene Braunwald et al., eds., pp. 491 762 (15th ed. 2001).

In certain embodiments, the target tissue is a tumor, e.g., a solid tumor or a tumor associated with soft tissue (e.g., soft tissue sarcoma), in a human. The tumor can be associated with cancers of (i.e., located in) the oral cavity and pharynx, the digestive system, the respiratory system, bones and joints (e.g., bony metastases), soft tissue, the skin (e.g., melanoma), breast, the genital system, the urinary system, the eye and orbit, the brain and nervous system (e.g., glioma), or the endocrine system (e.g., thyroid) and is not necessarily the primary tumor. Tissues associated with the oral cavity include, but are not limited to, the tongue and tissues of the mouth. Cancer can arise in tissues of the digestive system including, for example, the esophagus, stomach, small intestine, colon, rectum, anus, liver, gall bladder, and pancreas. Cancers of the respiratory system can affect the larynx, lung, and bronchus and include, for example, non-small cell lung carcinoma. Tumors can arise in the uterine cervix, uterine corpus, ovary vulva, vagina, prostate, testis, and penis, which make up the male and female genital systems, and the urinary bladder, kidney, renal pelvis, and ureter, which comprise the urinary system. The target tissue also can be associated with lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like).

The tumor can be at any stage, and can be undergoing treatment with one or more other therapies. The inventive method is useful in treating tumors (e.g., destruction of tumor cells or reduction in tumor size) that have been proven to be resistant to other forms of cancer therapy, such as radiation-resistant tumors. The tumor also can be of any size. Ideally, in treating the subject for cancer, the inventive method results in cancerous (tumor) cell death and/or reduction in tumor size. It will be appreciated that tumor cell death can occur without a substantial decrease in tumor size due to, for instance, the presence of supporting cells, vascularization, fibrous matrices, etc. Accordingly, while reduction in tumor size is preferred, it is not required in the treatment of cancer.

For the purposes of promoting an understanding of the principles of the disclosure, reference will now be made to the embodiments illustrated herein and specific language will be used to describe the same. It will nevertheless be understood that no limitation of the scope of the disclosure is thereby intended. Any alterations and further modifications in the described processes, systems or devices, and any further applications of the principles of the disclosure as described herein, are contemplated as would normally occur to one skilled in the art to which the invention relates.

The term "about" refers to a range of plus or minus 10 percent of the stated value. For example, the term "about 1.0" encompasses a range of value from 0.9 to 1.1.

The term "substantially free" means that a composition comprises less than 5% by weight of C-1a gentamicin, C-2a gentamicin, and/or C-2 gentamicin, for example, less than about 4% by weight, less than about 3% by weight, less than about 2% by weight, less than about 1% by weight, less than about 0.5% by weight, or less than about 0.1% by weight. In some embodiments, the composition does not comprise C-1a gentamicin or C-2a gentamicin.

The term "therapeutically effective amount" refers to an amount of a compound or formulation that when administered to a patient has a therapeutic or prophylactic effect on the patient. The therapeutic or prophylactic effect may be noticeable after a single dose of the compound of formulation or more commonly after a course of treatment with the compound or formulation, e.g., inhibiting growth of bacteria, promoting at least one aspect of cell cytotoxicity (e.g., inhibition of growth, inhibiting survival of a cancer cell, reducing proliferation, reducing size and/or mass of a tumor), or treatment, healing, prevention, delay of onset, halting, or amelioration of other relevant medical condition (s) associated with a particular bacterial infection, genetic disease, or cancer. The therapeutic or prophylactic effect observed in the subject can be to any suitable degree (10, 20, 30, 40, 50, 60, 70, 80, 90% or more). In some aspects, one or more symptoms of the bacterial infection, genetic disease, or cancer are prevented, reduced, halted, or eliminated subsequent to administration of C-1 gentamicin or a pharmaceutically acceptable acid addition salt thereof, thereby effectively treating the bacterial infection, genetic disease, or cancer to at least some degree.

The expression "gentamicin complex," "native gentamicin complex," or "native gentamicin" as used herein includes commercially available mixtures that comprise at least two, and preferably at least three, of the 4 congeners of gentamicin disclosed herein. For comparative purposes, a preferred gentamicin complex consists of C-1a gentamicin, C-1 gentamicin, and C-2 gentamicin in a ratio of 19.1:31.3:49.6, available from RAFA Laboratories Ltd. (Jerusalem, Israel).

The expression "consisting essentially of," as used herein in reference to the C-1 gentamicin composition, is intended to signify that such composition may contain trace amounts of the C-2a and/or C-1a gentamicin congeners, but that such amounts are less than that which would give rise to clinically significant nephrotoxicity. For example, in some embodiments, in a composition consisting essentially of C-1gentamicin, the amount of C-2a and/or C-1a gentamicin is generally less than about 5% by weight (e.g., less than about 3% by weight, less than about 2% by weight), and preferably less than about 1% by weight (e.g., less than about 0.5% by weight, less than about 0.2% by weight).

The term "total gentamicin" refers to the sum of all gentamicin congeners in a composition or sample, i.e., the sum of the C-1, C-1a, C-2, and C-2 congeners of gentamicin, which may be expressed, for example, as a concentration, such as mg/mL for a liquid, pharmaceutical composition or µg/mL for a cellular assay. When the word "gentamicin" is used without reference to one or more specific congeners, the term refers to "total gentamicin."

The free base as well as pharmaceutically acceptable acid addition salts of gentamicin as described herein can be employed in the practice of various aspects of the disclosure. The expression "pharmaceutically acceptable acid addition salt" is used herein to refer to a mono or poly salt formed by the interaction of one molecule of the gentamicin congener C-1 with one or more molecules of a pharmaceutically acceptable acid. Included among those acids are acetic, hydrochloric, sulfuric, maleic, phosphoric, nitric, hydrobromic, ascorbic, malic, and citric acid, and those other acids commonly used to make salts of amine-containing pharmaceuticals. Hydrophobic acids, such as fatty acids having at least eight carbon atoms, provide salts of reduced aqueous solubility. Salts of the gentamicin component with one or more pharmaceutically acceptable acids are suitable for use in a solution or suspension formulation, e.g., using a pharmaceutically acceptable carrier.

As used herein, the term "pharmaceutically acceptable carrier" includes any and all solvents, diluents, or other liquid vehicles, dispersion or suspension aids, surface active agents, isotonic agents, thickening or emulsifying agents, preservatives and the like, as suited to the particular dosage form desired. *Remington's Pharmaceutical Sciences,* 20th Edition, A. R. Gennaro (Williams and Wilkins, Baltimore, Md., 2000) discloses various carriers used in formulating pharmaceutical compositions and known techniques for the preparation thereof. Except insofar as any conventional carrier medium is incompatible with the compositions used to practice various aspects of the disclosure, such as by producing any undesirable biological effect or negatively affecting the stability of the gentamicin, its use is contemplated to be within the scope of this disclosure. Thus, solutions or suspensions of the gentamicin component described herein can also include a sterile diluent, such as water for injection, saline solution, fixed oils, polyethylene glycols, glycerin, propylene glycol or other synthetic solvents; antibacterial agents, such as benzyl alcohol or methyl parabens; antioxidants, such as ascorbic acid or sodium bisulfite; chelating agents, such as EDTA; buffers, such as acetates, citrates or phosphates; and agents for the adjustment of tonicity, such as sodium chloride or dextrose. A parenteral preparation of the compositions of the disclosure can be enclosed in ampoules, disposable syringes, or multiple dose vials made of glass or plastic, in accordance with standard practice in the field of the invention.

In some embodiments of the foregoing methods, administering comprises intravenous or intramuscular injection. The method can comprise subcutaneous injection. The method can comprise administering greater than about 1 mg/kg total gentamicin (i.e., 1 mg gentamicin per kg bodyweight of the subject), e.g., administering greater than about 1 mg/kg in either a single injection/infusion or during a time interval, such as an eight-hour interval. The method can comprise administering greater than about 1.5 mg/kg total gentamicin, such as greater than about 2 mg/kg total gentamicin, greater than about 2.5 mg/kg total gentamicin, greater than about 3 mg/kg total gentamicin, greater than about 3.5 mg/kg total gentamicin, greater than about 4 mg/kg total gentamicin, greater than about 4.5 mg/kg total gentamicin, or greater than about 5 mg/kg total gentamicin. For example, the method can comprise administering between about 1 mg/kg and about 5 mg/kg total gentamicin, such as between about 1.5 mg/kg and about 4.5 mg/kg gentamicin, about 2.0 mg/kg and about 4.0 mg/kg gentamicin, about 3.0 mg/kg and about 3.5 mg/kg gentamicin, about 0.5 mg/kg and about 3.0 mg/kg gentamicin, about 1.0 mg/kg and about 2.5 mg/kg gentamicin, or between about 1.5 mg/kg and about 2.0 mg/kg gentamicin. The method can comprise administering about 1 mg/kg gentamicin, about 1.5 mg/kg, about 2 mg/kg, about 2.5 mg/kg, about 3 mg/kg, about 3.5 mg/kg, about 4 mg/kg, about 4.5 mg/kg, or about 5 mg/kg gentamicin.

In some embodiments, the method comprises administering a loading dose of total gentamicin from about 1.0 mg/kg to about 5.0 mg/kg total gentamicin. In some embodiments, the method comprises administering a maintenance dose of total gentamicin from about 0.5 mg/kg to about 3.0 mg/kg gentamicin.

In some embodiments, administering comprises intravenous or intramuscular injection. The method can comprise administering greater than about 1 mg/kg C-1 gentamicin (i.e., 1 mg C-1 gentamicin per kg bodyweight of the subject), e.g., administering greater than about 1 mg/kg in either a single injection/infusion or during a time interval, such as an eight-hour interval. The method can comprise administering greater than about 1.5 mg/kg C-1 gentamicin, such as greater than about 2 mg/kg C-1 gentamicin, greater than about 2.5 mg/kg C-1 gentamicin, greater than about 3 mg/kg C-1 gentamicin, greater than about 3.5 mg/kg C-1 gentamicin, greater than about 4 mg/kg C-1 gentamicin, greater than about 4.5 mg/kg C-1 gentamicin, or greater than about 5 mg/kg C-1 gentamicin. For example, the method can comprise administering between about 1 mg/kg and about 5 mg/kg C-1 gentamicin, such as between about 1.5 mg/kg and about 4.5 mg/kg C-1 gentamicin, about 2.0 mg/kg and about 4.0 mg/kg C-1 gentamicin, about 3.0 mg/kg and about 3.5 mg/kg C-1 gentamicin, about 0.5 mg/kg and about 3.0 mg/kg C-1 gentamicin, about 1.0 mg/kg and about 2.5 mg/kg C-1 gentamicin, or between about 1.5 mg/kg and about 2.0 mg/kg C-1 gentamicin. The method can comprise administering about 1 mg/kg C-1 gentamicin, about 1.5 mg/kg, about 2 mg/kg, about 2.5 mg/kg, about 3 mg/kg, about 3.5 mg/kg, about 4 mg/kg, about 4.5 mg/kg, or about 5 mg/kg C-1 gentamicin.

In some embodiments, the method comprises administering a loading dose of C-1 gentamicin from about 1.0 mg/kg to about 5.0 mg/kg C-1 gentamicin. In some embodiments, the method comprises administering a maintenance dose of C-1 gentamicin from about 0.5 mg/kg to about 3.0 mg/kg C-1 gentamicin.

The method can comprise administering the composition 1, 2, or 3 times per day. For example, gentamicin (e.g., total or C-1 gentamicin) may be administered once every 12 hours or once every 8 hours. The method can comprise re-administering the composition comprising gentamicin (e.g., total or C-1 gentamicin). For example, the composition may be administered 1, 2, or 3, times a day, e.g., once a day, once every 12 hours, or once every 8 hours.

In some embodiments, the total amount of gentamicin administered (e.g., the total amount of total gentamicin or C-1 gentamicin administered) is adjusted (i.e., raised or lowered) based on factors such as overall health and specific concerns such as the health of the subject's kidneys.

The terms "subject" and "patient" as used interchangeably herein, and refer to a mammal. Mammals include, but are not limited to, the order Rodentia, such as mice and rats, and the order Lagomorpha, such as rabbits. It is preferred that the mammals are from the order Carnivora, including Felines (cats) and Canines (dogs). It is more preferred that the mammals are from the order Artiodactyla, including Ovis (sheep), Bovines (cows) and Porcines (pigs) or of the order Perissodactyla, including Equines (horses). It is most preferred that the mammals are of the order Primates, Ceboids, or Simioids (monkeys) or of the order Anthropoids (humans and apes). In especially preferred embodiments, the subject is a human or rat, most preferably a human.

In some embodiments, the subject can have kidney disease or be at risk for developing kidney disease. In some embodiments, the subject does not have kidney disease. In some embodiments, the subject has cystic fibrosis, Hurler syndrome, Scheie syndrome, Duchenne muscular dystrophy, or Becker muscular dystrophy. The subject may have cancer.

The invention is further illustrated by the following embodiments.

(1) A method for treating a bacterial infection in a subject, comprising administering to the subject a composition comprising C-1 gentamicin or a pharmaceutically acceptable acid addition salt thereof, wherein the composition is substantially free of C-1a gentamicin and/or C-2a gentamicin.

(2) A method for treating a genetic disease in a subject, comprising administering to the subject a composition comprising C-1 gentamicin or a pharmaceutically acceptable acid addition salt thereof, wherein the composition is substantially free of C-1a gentamicin and/or C-2a gentamicin, and wherein the genetic disease is cystic fibrosis, Hurler Syndrome, Scheie syndrome, Duchenne muscular dystrophy, Becker muscular dystrophy, nephrogenic diabetes insipidus, hemophilia, dystrophic epidermolysis bullosa, or Kabuki syndrome.

(3) A method for treating cancer in a subject, comprising administering to the subject a composition comprising C-1 gentamicin or a pharmaceutically acceptable acid addition salt thereof, wherein the composition is substantially free of C-1a gentamicin and/or C-2a gentamicin, wherein cells of the cancer comprise a premature stop codon in the open reading frame of a gene.

(4) The method of any one of embodiments (1)-(3), wherein the composition further comprises C-2 gentamicin or a pharmaceutically acceptable acid addition salt thereof.

(5) The method of any one of embodiments (1)-(3), wherein the composition is substantially free of C-1a gentamicin, C-2 gentamicin, and C-2a gentamicin.

(6) The method of any one of embodiments (1)-(5), wherein the composition has a ratio of C-1a gentamicin to C-1 gentamicin of less than 1:10 (w/w).

(7) The method of any one of embodiments (1)-(6), wherein the composition has a ratio of C-2a gentamicin to C-1 gentamicin of less than 1:10 (w/w).

(8) The method of any one of embodiments (1)-(7), wherein the composition has a ratio of C-1 gentamicin to total gentamicin of greater than 9:10 (w/w).

(9) The method of any one of embodiments (1)-(8), wherein the composition is a liquid, and the composition comprises C-1 gentamicin at a concentration between about 1 mg/mL and about 115 mg/mL.

(10) The method of any one of embodiments (1)-(9), wherein the composition is a liquid, and the composition comprises C-2 gentamicin at a concentration between about 1 mg/mL and about 115 mg/mL.

(11) The method of any one of embodiments (1)-(10), wherein the composition is a liquid, and the composition comprises less than 1000 ppm C-1a gentamicin.

(12) The method of any one of embodiments (1)-(11), wherein the composition is a liquid, and the composition comprises less than 1000 ppm C-2a gentamicin.

(13) The method of any one of embodiments (1)-(12), wherein the composition is a liquid, and administering comprises intravenous or intramuscular injection.

(14) The method of embodiment (13), comprising administering greater than about 1 mg/kg total gentamicin.

(15) The method of embodiment (14), comprising administering greater than about 2 mg/kg total gentamicin.

(16) The method of embodiment (14), comprising administering between about 1 mg/kg and about 5 mg/kg total gentamicin.

(17) The method of embodiment (16), comprising administering between about 1.5 mg/kg and about 4.5 mg/kg total gentamicin.

(18) The method of any one of embodiments (1)-(17), wherein the subject is rodent, lagomorph, feline, canine, ovine, porcine, bovine, equine, or primate.

(19) The method of embodiment (18), wherein the subject is a human.

(20) The method of any one of embodiments (1)-(19), further comprising administering at least one additional antibiotic to the subject.

(21) The method of any one of embodiments (1)-(20), wherein the C-1 gentamicin or a pharmaceutically acceptable acid addition salt thereof is administered in a therapeutically effective amount.

(22) A composition comprising C-1 gentamicin or a pharmaceutically acceptable acid addition salt thereof, a preservative, and a chelating agent, wherein the composition is a liquid, and the composition is substantially free of C-1a gentamicin and/or C-2a gentamicin.

(23) The composition of embodiment (22), wherein the composition comprises less than 1000 ppm C-1a gentamicin.

(24) The composition of embodiment (22) or (23), wherein the composition comprises less than 1000 ppm C-2a gentamicin.

(25) The composition of any one of embodiments (22)-(24), wherein the composition comprises C-1 gentamicin at a concentration between about 1 mg/mL and about 115 mg/mL.

The following examples further illustrate the invention but should not be construed as in any way limiting its scope.

EXAMPLES

Example 1

This example demonstrates the isolation and purification of specific congeners from native gentamicin in an embodiment of the invention.

Four gentamicin congeners were purified from native gentamicin using reverse phase HPLC. Briefly, native gentamicin was loaded onto a C18 column (250×4.60 mm) and separated using an acetonitrile gradient comprising 0.1% trifluoroacetic acid (vol/vol), thereby isolating the C-1, C-2, C-2a, and C-1a congeners (FIG. 1). There was no overlap between adjacent peaks. For all studies, the same lot of gentamicin was used, which ensured that the results obtained were independent of potential variation in the ratio of gentamicin components.

Example 2

This example demonstrates the bactericidal efficacy of the congeners of gentamicin in an embodiment of the invention.

Figure 2:
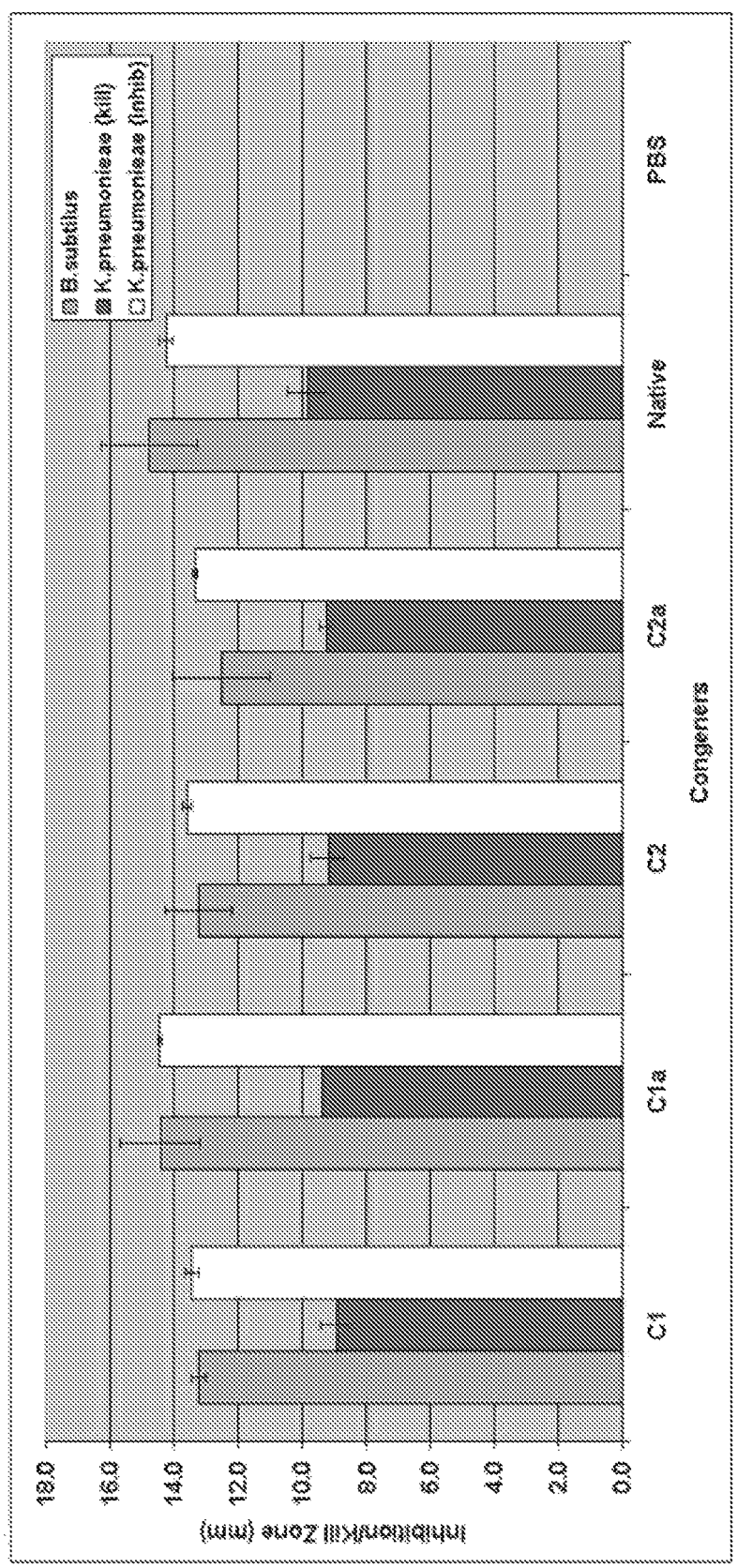
FIG. 2 is a graph illustrating the antibiotic activity of native gentamicin and the C-1, C-1a, C-2, and C-2a congeners of gentamicin against *Bacillus subtilis, Klebsiella pneumonia*, and a multi-drug resistant strain of *Klebsiella pneumoniae*.

The purified congeners of gentamicin of Example 1 each exhibited excellent bactericidal properties against both *Bacillus subtilis* and a multi-drug resistant form of *Klebsiella pneumonia* (FIG. 2). Bacterial assays were performed using native gentamicin and the C-1, C-1a, C-2, and C-2a congeners of gentamicin. The kill zones and growth inhibition zones were determined against three strains of bacteria: *Bacillus subtilis, Klebsiella pneumonia*, and a variant of *Klebsiella pneumonia* that exhibits multi-drug resistance. Native gentamicin and each congener of gentamicin demonstrated anti-bacterial activity against each bacterial strain.

Example 3

This example demonstrates the toxicity of native gentamicin, C-1a gentamicin, and C-2 gentamicin in rats in an embodiment of the invention.

Native gentamicin, C-2 gentamicin, C-1a gentamicin, and a saline control were each administered to three Sprague Dawley rats. Serum Creatinine ("SCr") was measured on days 0, 1, 2, 3, 5, 7, and 8 for rats given (a) mixed gentamicin congeners; (b) the purified C-2 congener at 99% purity; (c) the purified C-1a congener at 99% purity; and (d) saline injections (control). The results are displayed in Tables 1-8.

TABLE 1

100 mg/kg native gentamicin

| Rat | Day 0 | | Day 1 | | Day 2 | | Day 3 | | Day 5 | | Day 7 | |
|---|---|---|---|---|---|---|---|---|---|---|---|---|
| | Wt (g) | SCr (mg/dL) | Wt (g) | SCr (mg/dL) | Wt (g) | SCr (mg/dL) | Wt (g) | SCr (mg/dL) | Wt (g) | SCr (mg/dL) | Wt (g) | SCr (mg/dL) |
| 1 | 294 | 0.1 | 281 | 0.4 | 290 | 0.5 | 286 | 0.5 | 284 | 0.5 | 276 | 1.2 |
| 2 | 299 | 0.3 | 288 | 0.4 | 295 | 0.6 | 287 | 0.5 | 281 | 0.7 | 282 | 1.1 |
| 3 | 294 | 0.2 | 282 | 0.5 | 285 | 0.7 | 279 | 0.6 | 275 | 0.8 | 267 | 0.8 |
| Mean | 296 | 0.2 | 284 | 0.4 | 290 | 0.6 | 284 | 0.5 | 280 | 0.7 | 275 | 1.0 |

TABLE 2

100 mg/kg native gentamicin

| | Day 8 | |
|---|---|---|
| Rat | Wt (g) | SCr (mg/dL) |
| 1 | 279 | 1.3 |
| 2 | 284 | 1.0 |
| 3 | 280 | 0.8 |
| Mean | 281 | 1.0 |

TABLE 3

100 mg/kg C-2 gentamicin (99% pure)

| Rat | Day 0 | | Day 1 | | Day 2 | | Day 3 | | Day 5 | | Day 7 | |
|---|---|---|---|---|---|---|---|---|---|---|---|---|
| | Wt (g) | SCr (mg/dL) | Wt (g) | SCr (mg/dL) | Wt (g) | SCr (mg/dL) | Wt (g) | SCr (mg/dL) | Wt (g) | SCr (mg/dL) | Wt (g) | SCr (mg/dL) |
| 4 | 271 | 0.3 | 257 | 0.5 | 260 | 0.5 | 240 | 0.3 | 257 | 0.5 | 235 | 0.6 |
| 5 | 303 | 0.2 | 295 | 0.3 | 294 | 0.5 | 285 | 0.4 | 289 | 0.5 | 274 | 0.6 |
| 6 | 277 | 0.1 | 271 | 0.2 | 272 | 0.3 | 266 | 0.5 | 275 | 0.5 | 261 | 0.5 |
| Mean | 284 | 0.2 | 274 | 0.3 | 275 | 0.4 | 264 | 0.4 | 274 | 0.5 | 257 | 0.6 |

TABLE 4

100 mg/kg C-2 gentamicin (99% pure)

| | Day 8 | |
|---|---|---|
| Rat | Wt (g) | SCr (mg/dL) |
| 4 | 240 | 0.6 |
| 5 | 279 | 0.5 |
| 6 | 264 | 0.5 |
| Mean | 261 | 0.5 |

TABLE 5

100 mg/kg C-1a gentamicin (99% pure)
*Rat #8 died after the first injection

| | Day 0 | | Day 1 | | Day 2 | | Day 3 | | Day 5 | | Day 7 | |
|---|---|---|---|---|---|---|---|---|---|---|---|---|
| Rat | Wt (g) | SCr (mg/dL) | Wt (g) | SCr (mg/dL) | Wt (g) | SCr (mg/dL) | Wt (g) | SCr (mg/dL) | Wt (g) | SCr (mg/dL) | Wt (g) | SCr (mg/dL) |
| 7 | 310 | 0.2 | 305 | 0.5 | 295 | 0.5 | 283 | 0.4 | 290 | 0.6 | 286 | 0.6 |
| 8 | 293 | 0.2 | died | — | — | — | — | — | — | — | — | — |
| 9 | 290 | 0.1 | 282 | 0.3 | 273 | 0.4 | 265 | 0.5 | 265 | 0.5 | 249 | 0.6 |
| Mean | 298 | 0.2 | 293 | 0.4 | 284 | 0.5 | 274 | 0.5 | 278 | 0.6 | 268 | 0.6 |

TABLE 6

100 mg/kg C-1a gentamicin (99% pure)
*Rat #8 died after the first injection

| | Day 8 | |
|---|---|---|
| Rat | Wt (g) | SCr (mg/dL) |
| 7 | 293 | 0.6 |
| 8 | — | — |
| 9 | 252 | 0.7 |
| Mean | 273 | 0.7 |

TABLE 7

Saline (control)

| | Day 0 | | Day 1 | | Day 2 | | Day 3 | | Day 5 | | Day 7 | |
|---|---|---|---|---|---|---|---|---|---|---|---|---|
| Rat | Wt (g) | SCr (mg/dL) | Wt (g) | SCr (mg/dL) | Wt (g) | SCr (mg/dL) | Wt (g) | SCr (mg/dL) | Wt (g) | SCr (mg/dL) | Wt (g) | SCr (mg/dL) |
| 10 | 316 | 0.2 | 294 | 0.3 | 289 | 0.1 | 285 | 0.3 | 294 | 0.2 | 287 | 0.2 |
| 11 | 311 | 0.3 | 290 | 0.3 | 286 | 0.2 | 282 | 0.1 | 290 | 0.1 | 287 | 0.3 |
| 12 | 290 | 0.2 | 283 | 0.2 | 274 | 0.2 | 269 | 0.3 | 271 | 0.3 | 267 | 0.2 |
| Mean | 306 | 0.2 | 289 | 0.3 | 283 | 0.2 | 279 | 0.2 | 285 | 0.2 | 280 | 0.2 |

TABLE 8

Saline (control)

| | Day 8 | |
|---|---|---|
| Rat | Wt (g) | SCr (mg/dL) |
| 10 | 290 | 0.3 |
| 11 | 291 | 0.2 |
| 12 | 272 | 0.2 |
| Mean | 284 | 0.2 |

Example 4

This example demonstrates the toxicity of native gentamicin, C-1 gentamicin, C-1a gentamicin, and C-2a gentamicin in rats in an embodiment of the invention.

Figure 3:
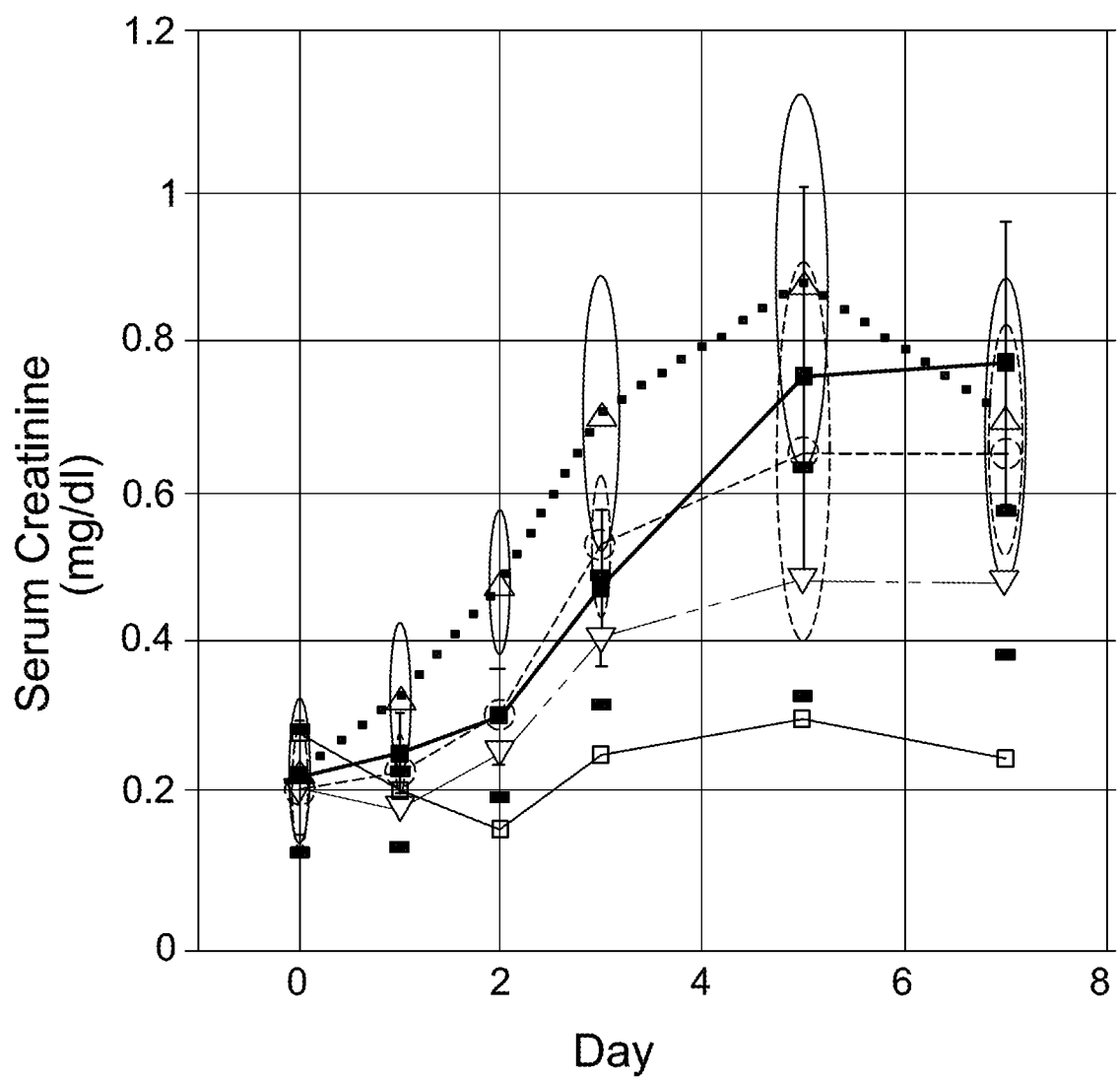
FIG. 3 is a graph illustrating serum creatinine levels in rats measured over 7 days after administering native gentamicin (■), saline (□), C-1 gentamicin (∇), C-1a gentamicin (○), or C-2a gentamicin (Δ).

In vivo toxicity studies were conducted on 22 rats with saline, native gentamicin, and the C-1, C-1a, and C-2a congeners of gentamicin. Serum Creatinine ("SCr") was measured at days 0, 1, 2, 3, 5, and 7 (FIG. 3; Tables 9-13). In some cases, the C-1 congener was found to be less toxic in vivo than the C-2 congener (compare Table 3 with Table 11), and the C1 congener displayed the lowest level of serum creatinine for any gentamicin congener administered during the rat studies.

TABLE 9

Saline Injections.

| Rat | Day 0 Wt (g) | Day 0 SCr (mg/dL) | Day 1 Wt (g) | Day 1 SCr (mg/dL) | Day 2 Wt (g) | Day 2 SCr (mg/dL) | Day 3 Wt (g) | Day 3 SCr (mg/dL) | Day 5 Wt (g) | Day 5 SCr (mg/dL) | Day 7 Wt (g) | Day 7 SCr (mg/dL) |
|---|---|---|---|---|---|---|---|---|---|---|---|---|
| 1 | 285 | 0.2 | 279 | 0.2 | 277 | 0.2 | 269 | 0.2 | 272 | 0.3 | 277 | 0.2 |
| 2 | 274 | 0.3 | 268 | .02 | 264 | .02 | 255 | 0.3 | 256 | 0.3 | 254 | 0.3 |
| 3 | 289 | 0.3 | 286 | 0.2 | 282 | 0.1 | 272 | 0.3 | 270 | 0.3 | 265 | 0.2 |
| 4 | 275 | 0.3 | 261 | 0.3 | 275 | 0.1 | 268 | 0.2 | 266 | 0.3 | 266 | 0.3 |
| Mean | 281 | 0.3 | 274 | 0.2 | 275 | 0.2 | 266 | 0.3 | 266 | 0.3 | 266 | 0.3 |

TABLE 10

Native gentamicin.

| Rat | Day 0 Wt (g) | Day 0 SCr (mg/dL) | Day 1 Wt (g) | Day 1 SCr (mg/dL) | Day 2 Wt (g) | Day 2 SCr (mg/dL) | Day 3 Wt (g) | Day 3 SCr (mg/dL) | Day 5 Wt (g) | Day 5 SCr (mg/dL) | Day 7 Wt (g) | Day 7 SCr (mg/dL) |
|---|---|---|---|---|---|---|---|---|---|---|---|---|
| 5 | 261 | 0.2 | 258 | 0.2 | 254 | 0.3 | 255 | 0.3 | 252 | 0.4 | 251 | 0.5 |
| 6 | 276 | 0.3 | 270 | 0.3 | 273 | 0.3 | 263 | 0.4 | 268 | 0.7 | 271 | 0.8 |
| 7 | 285 | 0.2 | 278 | 0.2 | 274 | 0.2 | 263 | 0.6 | 276 | 1.2 | 275 | 0.9 |
| 8 | 284 | 0.3 | 282 | 0.3 | 278 | 0.3 | 269 | 0.5 | 274 | 0.7 | 272 | 1.0 |
| 9 | 280 | 0.2 | 274 | 0.2 | 280 | 0.4 | 272 | 0.5 | 279 | 0.7 | 282 | 0.8 |
| 10 | 272 | 0.1 | 268 | 0.3 | 267 | 0.3 | 263 | 0.5 | 272 | 0.8 | 272 | 0.6 |
| Mean | 276 | 0.2 | 272 | 0.3 | 271 | 0.3 | 264 | 0.5 | 270 | 0.8 | 271 | 0.8 |

TABLE 11

C-1 congener.

| Rat | Day 0 Wt (g) | Day 0 SCr (mg/dL) | Day 1 Wt (g) | Day 1 SCr (mg/dL) | Day 2 Wt (g) | Day 2 SCr (mg/dL) | Day 3 Wt (g) | Day 3 SCr (mg/dL) | Day 5 Wt (g) | Day 5 SCr (mg/dL) | Day 7 Wt (g) | Day 7 SCr (mg/dL) |
|---|---|---|---|---|---|---|---|---|---|---|---|---|
| 11 | 256 | 0.2 | 243 | 0.2 | 240 | 0.3 | 233 | 0.4 | 250 | 0.4 | 250 | 0.4 |
| 12 | 272 | 0.2 | 260 | 0.2 | 265 | 0.2 | 256 | 0.3 | 272 | 0.3 | 275 | 0.4 |
| 13 | 256 | 0.3 | 253 | 0.1 | 255 | 0.3 | 245 | 0.5 | 260 | 0.6 | 264 | 0.5 |
| 14 | 286 | 0.1 | 269 | 0.2 | 262 | 0.2 | 256 | 0.4 | 265 | 0.6 | 269 | 0.6 |
| Mean | 268 | 0.2 | 256 | 0.2 | 256 | 0.3 | 248 | 0.4 | 262 | 0.5 | 265 | 0.5 |

TABLE 12

C-1a congener.

| Rat | Day 0 Wt (g) | Day 0 SCr (mg/dL) | Day 1 Wt (g) | Day 1 SCr (mg/dL) | Day 2 Wt (g) | Day 2 SCr (mg/dL) | Day 3 Wt (g) | Day 3 SCr (mg/dL) | Day 5 Wt (g) | Day 5 SCr (mg/dL) | Day 7 Wt (g) | Day 7 SCr (mg/dL) |
|---|---|---|---|---|---|---|---|---|---|---|---|---|
| 15 | 277 | 0.3 | 268 | 0.2 | 264 | 0.3 | 256 | 0.5 | 271 | 1.0 | 266 | 0.9 |
| 16 | 285 | 0.2 | 278 | 0.2 | 276 | 0.3 | 262 | 0.4 | 282 | 0.4 | 274 | 0.5 |
| 17 | 274 | 0.2 | 260 | 0.2 | 256 | 0.3 | 247 | 0.6 | 262 | 0.6 | 239 | 0.6 |
| 18 | 276 | 0.1 | 262 | 0.3 | 265 | 0.3 | 259 | 0.6 | 272 | 0.6 | 267 | 0.6 |
| Mean | 278 | 0.2 | 267 | 0.2 | 265 | 0.3 | 256 | 0.5 | 272 | 0.7 | 262 | 0.7 |

TABLE 13

| | C-2a congener. | | | | | | | | | | | |
|---|---|---|---|---|---|---|---|---|---|---|---|---|
| | Day 0 | | Day 1 | | Day 2 | | Day 3 | | Day 5 | | Day 7 | |
| Rat | Wt (g) | SCr (mg/dL) | Wt (g) | SCr (mg/dL) | Wt (g) | SCr (mg/dL) | Wt (g) | SCr (mg/dL) | Wt (g) | SCr (mg/dL) | Wt (g) | SCr (mg/dL) |
| 19 | 266 | 0.2 | 257 | 0.2 | 253 | 0.4 | 252 | 0.6 | 265 | 0.6 | 263 | 0.5 |
| 20 | 234 | 0.1 | 229 | 0.3 | 222 | 0.4 | 221 | 0.5 | 242 | 0.8 | 225 | 0.9 |
| 21 | 260 | 0.3 | 248 | 0.4 | 249 | 0.5 | 241 | 0.8 | 242 | 1.2 | 232 | 0.6 |
| 22 | 281 | 0.3 | 266 | 0.4 | 270 | 0.6 | 262 | 0.9 | 276 | 0.9 | 273 | 0.8 |
| Mean | 260 | 0.2 | 250 | 0.3 | 249 | 0.5 | 244 | 0.7 | 256 | 0.9 | 248 | 0.7 |

Example 5

This example demonstrates the toxicity of native gentamicin and C-1, C-1a, C-2, and C-2a gentamicin in yeast in an embodiment of the invention.

Figure 4:
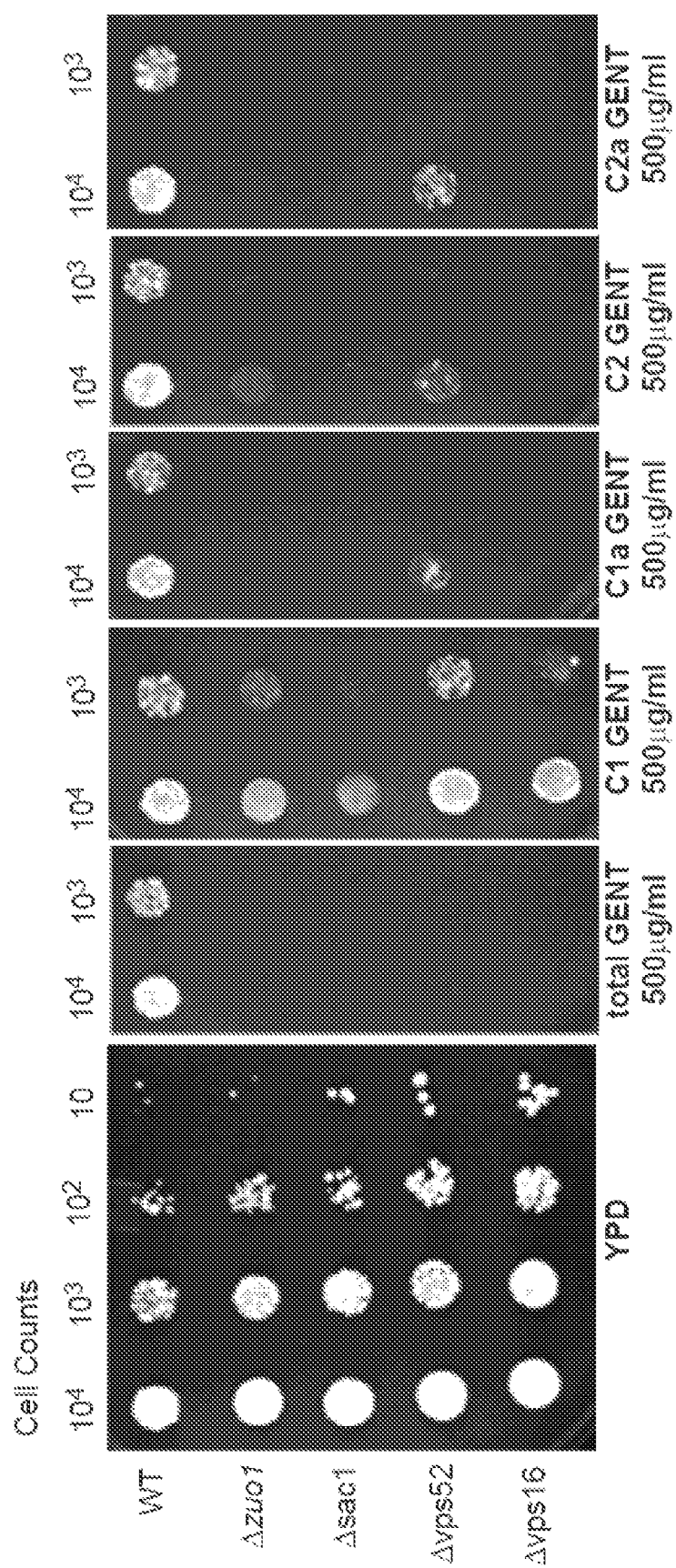
FIG. 4 is a series of photomicrographs showing the effect of native gentamicin ("total GENT") and gentamicin congeners C-1, C-1a, C-2 and C-2a on the growth of a variety of yeast strains that are sensitive to gentamicin toxicity.

The toxicity of native gentamicin and the C-1, C-1a, C-2, and C-2a congeners of gentamicin was tested in a strain of mutant yeast which is known to be sensitive to gentamicin. The growth of the wild type, Δzuo1, Δsac1, Δvsp52, and Δvps16 strains of *Saccharomyces cerevisiae* was determined by measuring cell counts for yeast exposed to no gentamicin ("YPD") and to each of the following conditions: 500 μg mL$^{-1}$ native gentamicin ("total GENT"), 500 μg mL$^{-1}$ C-1 gentamicin, 500 μg mL$^{-1}$ C-1a gentamicin, 500 μg mL$^{-1}$ C-2 gentamicin, and 500 μg mL$^{-1}$ C-2a gentamicin. FIG. 4 shows photographs of the growth tests conducted with each strain of yeast, which indicate that C-1 gentamicin has less of an effect on yeast growth than native gentamicin or any of the other congener of gentamicin.

Example 6

This example demonstrates the toxicity of native gentamicin and C-1, C-1a, C-2, and C-2a gentamicin in bovine cells in an embodiment of the invention.

Figure 5:
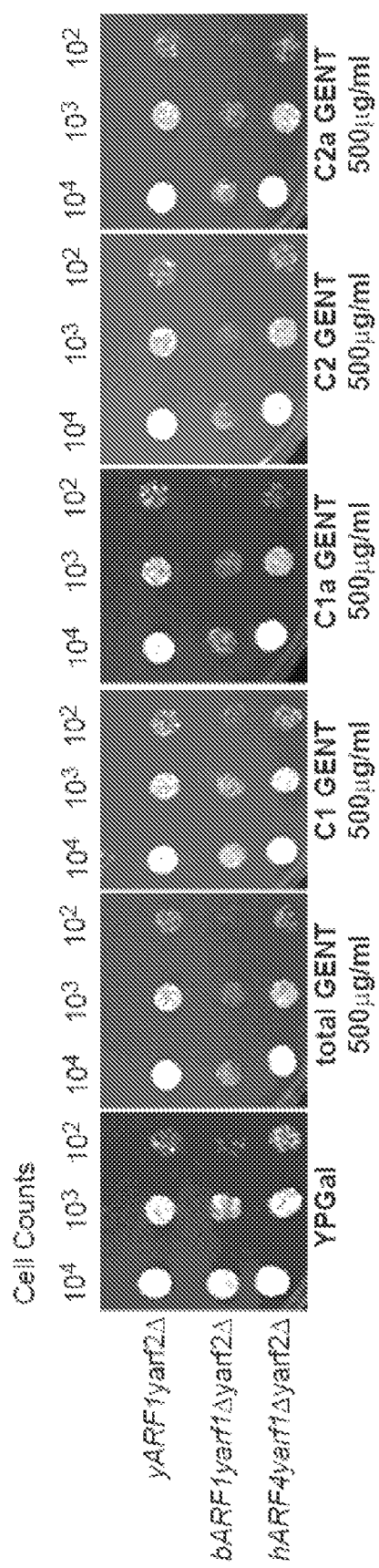
FIG. 5 is a series of photomicrographs showing the effect of native gentamicin ("total GENT") and gentamicin congeners C-1, C-1a, C-2, and C-2a on the growth of certain bovine cells.

The toxicity of native gentamicin and the C-1, C-1a, C-2, and C-2a congeners of gentamicin was tested in bovine cells. Specifically, the growth of yARF1yarf2Δ, yARF1yarf2Δ, and yARF1yarf2Δ cells was determined by measuring cell counts for bovine cells exposed to no gentamicin ("YPGal") and to each of the following conditions: 500 μg mL$^{-1}$ native gentamicin ("total GENT"), 500 μg mL$^{-1}$ C-1 gentamicin, 500 μg mL$^{-1}$ C-1a gentamicin, 500 μg mL$^{-1}$ C-2 gentamicin, and 500 μg mL$^{-1}$ C-2a gentamicin. FIG. 5 shows photographs of the growth tests conducted with bovine cells, which indicate that C-1 gentamicin has less of an effect on bovine cell growth than native gentamicin or any of the other congeners of gentamicin.

Figure 6:
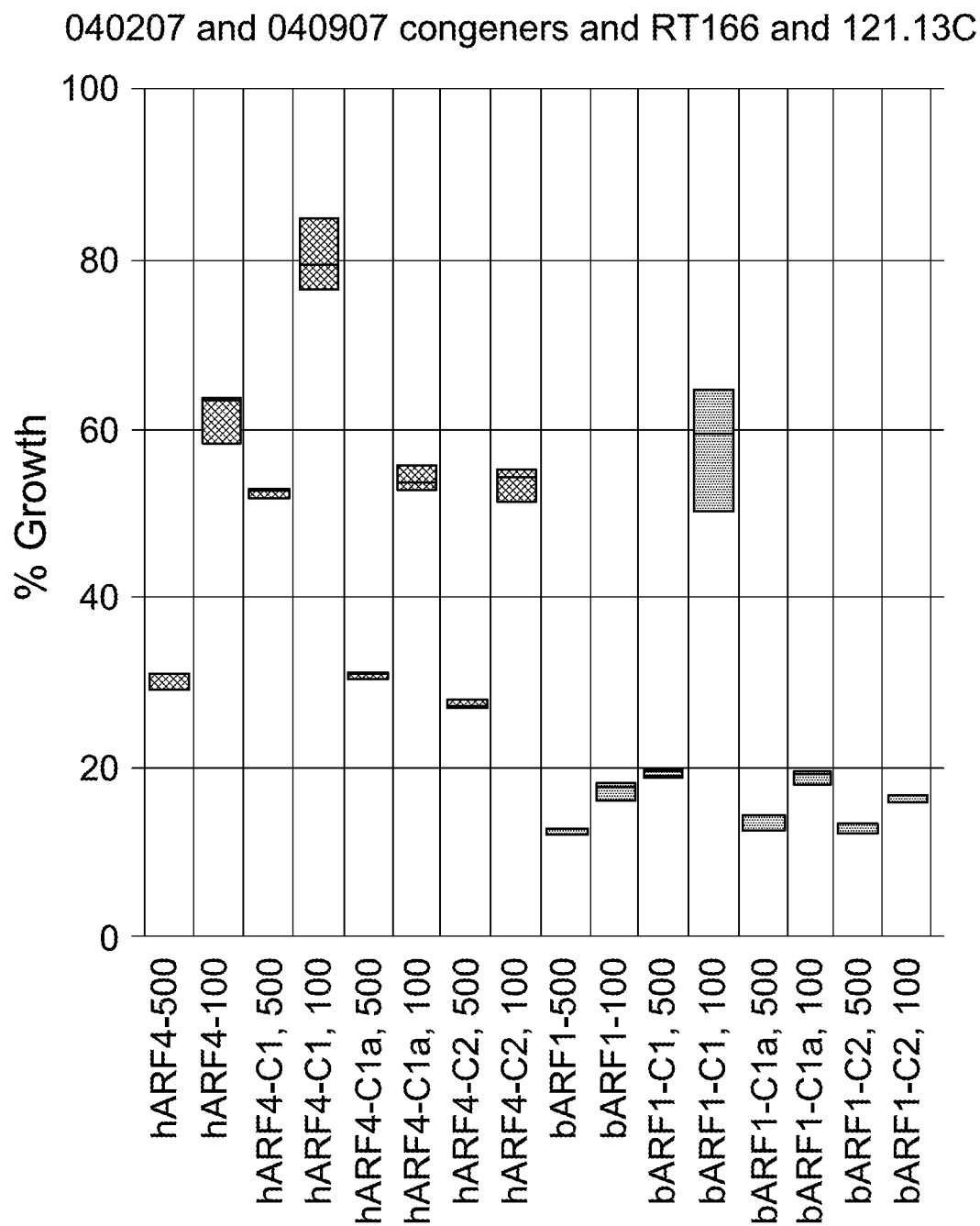
FIG. 6 is a plot illustrating the effect of native gentamicin, C-1 gentamicin, C-1a gentamicin, and C-2 gentamicin on the growth of hARF4 and bARF1 bovine cells.

FIG. 6 illustrates the effect of different congeners of gentamicin on the growth of hARF4 and bARF1 cells. Growth of these cells was measured in the presence of either 100 μg mL$^{-1}$ or 500 μg mL$^{-1}$ native gentamicin (hARF4-100; hARF4-500; bARF1-100; and bARF1-500); C-1 gentamicin (hARF4-C1, 100; hARF4-C1, 500; bARF1-C1, 100; and bARF1-C1; 500); C-1a gentamicin (hARF4-C1a, 100; hARF4-C1a, 500; bARF1-C1a, 100; and bARF1-C1a, 500); C-2 gentamicin (hARF4-C2, 100; hARF4-C2, 500; bARF1-C2, 100; and bARF1-C2, 500); and C-2a gentamicin (data not shown). Cells exposed to 100 μg mL$^{-1}$ of C-1 gentamicin (hARF4-C1, 100; bARF-C1, 100) exhibited higher percent growth relative to other congeners of gentamicin or native gentamicin. Similarly, cells exposed to 500 μg mL$^{-1}$ of C-1 gentamicin (hARF4-C1, 500; bARF-C1, 500) exhibited higher percent growth relative to cells exposed to 500 μg mL$^{-1}$ of other congeners of gentamicin or 500 μg mL$^{-1}$ of native gentamicin.

Example 7

This example demonstrates the effects of gentamicin on stop codon readthrough in an embodiment of the invention.

Native gentamicin and various congeners prepared as in Example 1 were tested to determine their effect on stop codon readthrough. Briefly, the percentage of readthrough of the stop codon UGAC was measured after exposure to C-1 gentamicin, C-2 gentamicin, or native gentamicin.

A plasmid including hCFTR-G542X under control of the rat FABP promoter was derived from a FABP-hCFTR-WT plasmid. The G542X premature stop mutation was introduced by the direct exchange of a 3043 bp BspEI/NcoI fragment from pDB436, yielding the FABP-CFTR-G542X plasmid pDB488. In addition to the G542X mutation, this plasmid contains an additional SalI restriction site that was introduced at codon 764 of the CFTR cDNA. This new restriction site does not alter the amino acid sequence of the CFTR protein.

In order to determine the optimal concentrations of the aminoglycosides (tobramycin, amikacin, and gentamicin) to use in the mammalian translation system, increasing amounts of each aminoglycoside were added to a rabbit reticulocyte translation system while expressing the QX(N) (UGAC) construct. The effect of aminoglycosides on total protein synthesis was monitored by comparing the total amount of proteins synthesized in the presence and absence of various aminoglycosides. A range of aminoglycoside concentrations was then determined that allowed a maximal amount of termination suppression without inhibiting total protein synthesis more than two- to threefold. In vitro translation reactions were carried out using the TNT coupled transcription/translation system (Promega, Madison, Wis.). Each reaction was carried out in a total volume of 12.625 μl and contained: 6.25 μl reticulocyte lysate, 0.625 μl 20×TNT reaction buffer, 2.5 μl 20 mM rNTPs, 0.25 μl 1 mM amino acids (minus methionine), 1.0 μl [$^{35}$S]methionine (11 μCi/μl NEN-Dupont, Boston, Mass.), 0.25-μl 40 U/μl RNAsin inhibitor (Promega, Madison, Wis.), 0.25-μl 80 U/μl SP6 RNA polymerase (Promega, Madison, Wis.), 1.0 μl 1 mg/ml DNA template, 0.5 μl H$_2$O, tobramycin, amikacin (CAL-BIOCHEM™, EMD Millipore, Billerica, Mass.), or gentamicin (GIBCO™, Life Technologies, Grand Island, N.Y.). The mixture was incubated for 2 h at 30° C., 12.6 μl of sodium dodecyl sulfate sample buffer was added to each reaction, and the samples were boiled. Then 1-2 μl of each sample was loaded onto a 12.5% sodium dodecyl sulfate polyacrylamide gel. The gel was dried and subjected to PhosphorImager analysis in order to quantitate the amount of truncated and full-length protein species. The percentage of readthrough was then calculated as the amount of full-length protein/(truncated+full-length species)×100%.

Foci assays were carried out as follows. Rat embryo fibroblast (REF) cells were obtained from American Type Culture Collection (# CRL-1764) and cultured in Dulbecco's modified Eagle's medium supplemented with 10% fetal calf serum at 37° C. with 5% $CO_2$. An H-ras construct containing the dominant-negative mutation G12V was provided by Dr. Michael Cole, Princeton University. A 6.6-kb BamHI fragment containing the H-ras cDNA was subcloned into pcDNA3.1 Zeo (INVITROGEN™, Life Technologies, Grand Island, N.Y.) under cytomegalovirus promoter control. The murine genomic p53 construct, long terminal repeat (LTR)-p53val, contained an A135V mutation and was expressed under LTR promoter control. This construct was generously provided by Dr. Michael Ruppert, University of Alabama at Birmingham. The R210X mutation was introduced into LTR-p53val by site-directed mutagenesis. The REF cells were transfected at 60-70% confluency in a six well (35 $mm^2$ per well) culture dish with the indicated plasmids using 2 μg total DNA and 8 μl lipofectamine (GIBCO™ BRL, Life Technologies, Grand Island, N.Y.) for 4 h in the presence of sera. Aminoglycosides were added 24 h after the transfection. For these experiments 200 μg/ml of either C-1 gentamicin (drug 1), non-toxic C-2 gentamicin (drug 2), or native gentamicin (drug 3) were added. Foci began to form approximately 2-3 days after the reference cells reached confluency, and the number of foci in each 35 $mm^2$ well was determined in a blinded manner. A lacZ gene was subcloned into the pcDNA3.1 Zeo plasmid and used as a transfection control with β-galactosidase staining.

Figure 7:
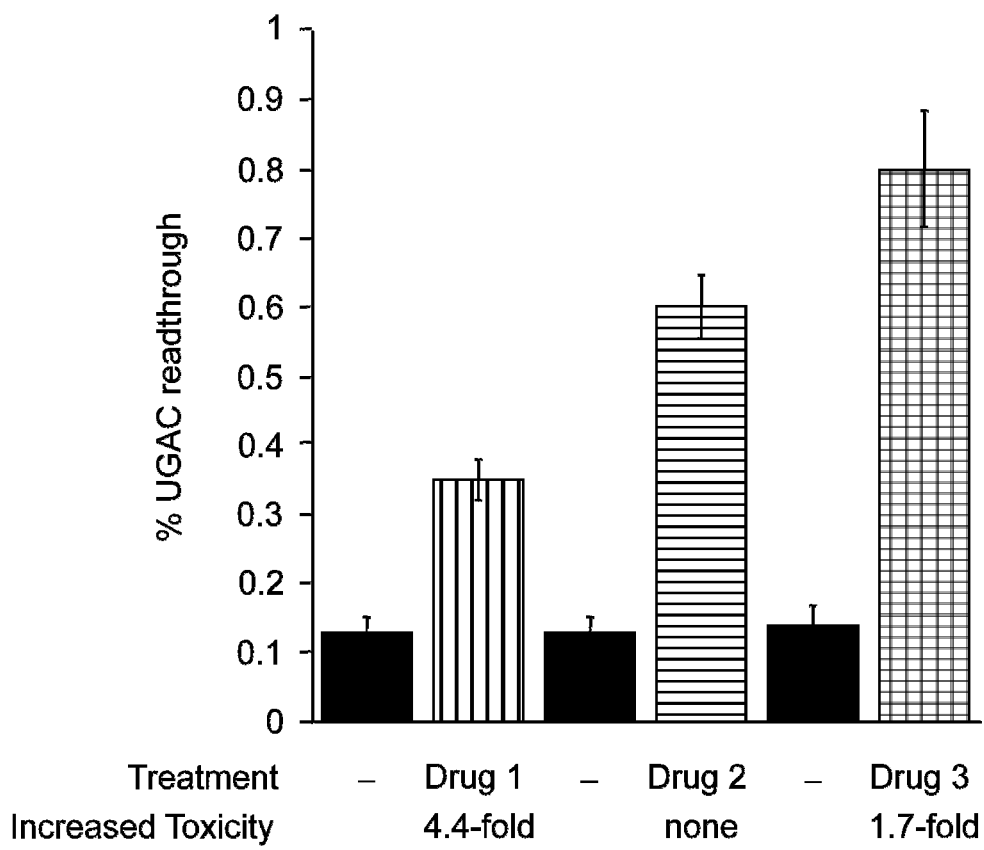
FIG. 7 is a graph illustrating the effect of C-1 gentamicin (labeled drug 1); C-2 gentamicin (labeled drug 2); and native gentamicin (labeled drug 3) on readthrough of the UGAC stop codon. The cells were exposed to 200 µg mL$^{-1}$ of each compound for 24 hours.

The results of these tests are summarized in FIG. 7. C-1 gentamicin, C-2 gentamicin, and native gentamicin each exhibited greater readthrough relative to controls. Moreover, C-1 gentamicin (drug 1) exhibited 4.4-fold increased toxicity relative to the control (no drug), whereas native gentamicin (drug 3) only had 1.7-fold increased toxicity and C-2 gentamicin (drug 2) had no increased toxicity (FIG. 7).

Example 8

This example demonstrates a prophetic alternative method of determining the effects of gentamicin on PTC (e.g., TAA, TAG, TGA) readthrough using a fluorescence resonance energy transfer (FRET) probe in an embodiment of the invention.

Figure 8:
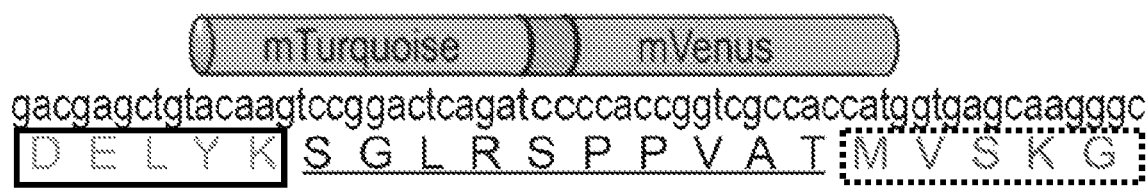
FIG. 8 is illustrates the fluorescence resonance energy transfer (FRET) probe that uses a Turquoise-10AA-Venus plasmid and shows the amino acid (AA) sequence (SEQ ID NO: 12) and corresponding DNA sequence (SEQ ID NO: 11) to be placed at the end of Turquoise (solid boxed text), a 10AA linker (underlined), and before the beginning of Venus (dashed boxed text). The tcc of SEQ ID NO: 11 are the nucleotides that will be altered using site-directed mutagenesis.

Normal human proximal tubule kidney (NHPTK) cells will be transfected with the plasmid of a particular genetic disease (Table 14) using the AMAXA™ electroporation procedure (Lonza Inc., Basel, Switzerland) on day 1 to provide a disease-specific stop codon. On day 2 gentamicin will be added. A dose response (0 to 1.0 mg/ml) will be performed to define the level of fluorescence resonance energy transfer (FRET) achieved while monitoring cell death using a SYTOX™ Red (Thermo Fisher Scientific, Waltham, Mass.) viability measurement. FIG. 8 illustrates the FRET probe to be used, in which the Turquoise-10AA-Venus plasmid has the unique property of following stop codon readthrough by monitoring FRET in both cultured cells and animals (Tao et al., *Am J Physiol,* 309(11), C724-35 (Dec. 1, 2015). This probe is ideal for two reasons. First, its high FRET efficiency will provide an excellent quantitative readout. Second, in the absence of PTC suppression, the Turquoise fluorescence will serve as the marker for plasmid delivery thus ensuring the correct cells are being studied and allowing for sensitive ratiometric analysis. FIG. 8 details the amino acid and DNA sequence to be placed at the end of Turquoise (donor; solid boxed text), a 10AA linker (underlined text), and before the beginning of Venus (acceptor; dashed boxt text). The tcc are the nucleotides that will be altered to taa, tag, and tga using site-directed mutagenesis and readthrough will be evaluated for no gentamicin, total gentamicin, C-1 gentamicin, C-1a gentamicin, C-2 gentamicin, and C-2a gentamicin. All plasmids will be verified by sequencing prior to usage. Depending upon the disease-related stop codon targeted for readthrough, some level of toxicity may be acceptable and still provide interpretable positive benefits. Each unique stop codon analyzed will have its gentamicin congener-induced PTC suppression, i.e., FRET, normalized to its FRET efficiency in the absence of any gentamicin. Based on previous studies, it is anticipated that a gentamicin concentration between 100-800 μg/ml will be optimal for monitoring readthrough with gentamicin with an incubation time of between 12-48 h providing a quantifiable read out. The specific steps of the assay will be:

1. NHPTK cells will be grown to 70-80% confluence in a T75 flask.
2. Cells will be transfected using either the AMAXA™ (Lonza Inc., Basel, Switzerland) or LIPOFECTAMINE™ (Thermo Fisher Scientific, Waltham, Mass.) method.
3. Cells will be plated onto a flat bottom, tissue culture (TC) treated, black 96 well plate at a density of $2 \times 10^4$ cells/well.
4. On day 2, plates will be washed with fresh media and gentamicin-containing media added to appropriate wells. Concentrations to be compared are 0, 100, 200, 500, and 1000 μg/ml.
5. Prior to measuring FRET, an aliquot of SYTOX™ Red Dead cell stain (Invitrogen, Carlsbad, Calif.) can be added to a final concentration of 5 nM, and cells are incubated for an additional 15 minutes. Post gentamicin addition time points will be compared at 12, 24, and 48 hours.
6. Fluorescence will be read using the CLARIOSTAR™ plate reader (BMG Labtech, Ortenberg, Germany) which will permit both FRET and SYTOX™ Red monitoring in 2 separate steps. First Turquoise (donor) (excitation/emission of 434/474), and Venus (acceptor) (excitation/emission 515/528) fluorescence will be quantified followed by SYTOX™ Red (excitation/emission of 633/660). SYTOX™ Red is used for dead cell monitoring.
7. To control for any cell number variability between wells, Hoechst 33342 will be added to 1-5 μg/ml for 1 hr followed by reading of fluorescence (excitation/emission 350/460). Hoeschst 33342 is used for total cell quatification.
8. Conditions will be repeated in quadruplicate and studies repeated 3 times.

Disease-specific stop codons and surrounding nucleotides to be evaluated and inserted between Turquoise (donor) and Venus (acceptor) are set forth in Table 14. The first set of mutations target Duchene muscular dystrophy (DMD) and represent premature stop codon mutations that were shown to have significant gentamicin induced suppression using a dual gene reporter system in NIH3T3 cells (Bidou, et al., *Gene Ther.,* 11, 619-27 (2004)). The second disease stop codon that will be evaluated is caused by null mutations in the leukemia inhibitory factor receptor gene (LIFR). Gentamicin was shown to induce trace amounts of functional LIFR protein though toxicity occurred at higher doses (Bellais et al., *Eur. J. Hum. Genet.*, 18, 130-2 (2010)). Consequently, the identification of a nontoxic gentamicin could prove very beneficial for some of these patients. The third disease to be targeted is colorectal cancer. The adenomatous polyposis coli (APC) protein is abnormal in approximately 85% of all sporadic and hereditary colorectal tumors (Zilberberg et al., *Gut,* 59, 496-507 (2010)). The fourth disease to be targeted is the TP53 tumor suppressor gene, p53, which is mutated in >50% of human cancers with nonsense mutations accounting for 8% (Floquet et al., *Nucleic Acids Res.* 39, 3350-62 (2011); and Bykov et al., *FEBS Lett.*, 588, 2622-7 (2014)). p53 acts as a cell regulator of growth, cell division and apoptosis. When mutated by a PTC in tumor cells there is uncontrolled cell division. Introducing wtp53 or increasing PTC suppression for production of wtp53 has been shown to reduce tumor cell growth. The 2 stop codon regions with the highest level of gentamicin-induced PTC suppression when analyzed in a cell based assay will be studied. The final disease to be targeted is cystic fibrosis (CF), caused by mutations in the CF transmembrane conductance regulator (CFTR) gene that encodes a chloride ion channel. Most mutations in CFTR are point mutations with premature sequence termination resulting in 18% of the mutations (Zeitlin, P. L., *J. Clin. Invest.*, 103, 447-52 (1999)). The most common premature stop codon mutation in CF patients, G542X, will be studied.

TABLE 14

Duchenne muscular dystrophy

| 1143d (wtQ, CAA) | GAT CAC ATG TGC TAA CAG GTC TAT GCC | SEQ ID NO: 1 |
| 2522d (wtQ, CAG) | CAG GAT TTG GAA TAG AGG CGT CCC AGT | SEQ ID NO: 2 |
| 319d (wtS, TCA) | AGC CCA TTT CCT TGA CAG CAT TTG GAA | SEQ ID NO: 3 |
| MDX (wtQ, CAA) | TTG AAA GAG CAA TAA AAT GGC TTC AAC | SEQ ID NO: 4 |

Stuve-Wiedemann Syndrome

| R597X (wtR,AGA) | CAC AAA GCA GAG ATA TGA CTT GAT AAG | SEQ ID NO: 5 |
| R812X (wtR,AGA) | AGT TAC CAC CTG GTC TTG TGA GCC TAT ACA | SEQ ID NO: 6 |

Colorectal cancer
(*Adenomatous polyposis coli*, APC)

| R1450X (wtR, CGA) | GCT CAA ACC AAG TGA GAA GTA CCT AAA AAT | SEQ ID NO: 7 |

TP53 tumor suppressor

| Q192X (wtQ, CAG) | CTG GCC CCT CCT TAG CAT CTT ATC | SEQ ID NO: 8 |
| R213X (wtR, CGA) | AGA AAC ACT TTT TGA CAT AGT GTG | SEQ ID NO: 9 |

CFTR

| G542X (wtG, GGA) | AAT ATA GTT CTT GGA GAA GGT GGA ATC | SEQ ID NO: 10 |

Example 9

This example demonstrates a prophetic example of an in vivo rat kidney PTC suppression assay in an embodiment of the invention.

Munich Wistar female (MW) Rats (150-200 g) will undergo hydrodynamic delivery of individual FRET plasmid. The congeners will be evaluated against the stop codons provided in Table 14. The use of MW rats, which have surface glomeruli (Dickson et al., *J. Am. Soc. Nephrol.* 25, 443-53 (2014)) will permit imaging of the S1 region of the proximal tubule. This segment of the proximal tubule is the most active in endocytosis and thus will provide the best FRET signal when determining gentamicin's efficiency of PTC suppression.

Intraperitoneal delivery of gentamicin will be started 7-10 days after hydrodynamic delivery of plasmid. This provides adequate recovery time while still having little, if any, drop off in transgene expression (Corridon et al., Am. *J. Physiol. Renal Physiol.* 304, F1217-29 (2013)). A single IP dose of gentamicin will be given for 2 consecutive days. Three concentrations of gentamicin (20, 50, and 100 mg/kg) will be studied. The disease-specific in vivo studies will use 100 mg/kg of each gentamicin compound. Intravital imaging of the kidney will be conducted 24 h after the second gentamicin injection.

Example 10

This example demonstrates a prophetic evaluation of PTC suppression in tissue using nontoxic gentamicin congeners in an embodiment of the invention.

Transgenic mice will be administered nontoxic gentamicin congener intraperitoneally (IP) for 7 days at 3 doses (17, 34, and 68 mg/kg). Mice will be euthanized, tissue rapidly removed, and FRET quantified using 2-photon microscopy and the FRET probe of FIG. 8. This approach will enable fluorescence in tissues to be captured quickly and without any fixation or processing. Infusion of a nuclear dye that does not interfere with the FRET signal can also be used, if necessary, to facilitate better identification of cells. Imaging time will be limited to <15 minutes, which will enable adequate time to capture and evaluate fluorescence in 1-3 tissues, those not being imaged will be held in cold phosphate buffered saline (PBS). A piece of tissue not being imaged will be quick frozen for tissue homogenization that can be assayed by Western blot techniques to monitor and compare expression. If readthrough occurs, mTurquoise and mVenus will produce a distinct band of ~55 kDa versus ~25 kDa if no readthrough occurs. Adult organ tissues (e.g., bladder, bone, brain, epididymis, fat, heart, intestine, kidney, liver, lung, skeletal muscle, pancreas, prostate, seminal vesicles, skin, spleen, testes, tail) will be removed and imaged. To monitor for any nephrotoxicity, serum creatinine and kidney histology will also be evaluated. Based on level of FRET and nephrotoxicity higher doses and times may be explored.

To further evaluate whether PTC suppression in the tissue occurs, the tissue will be placed in optimal cutting temperature (OCT) medium to acclimate then transferred to a cryomold in fresh OCT, oriented, and frozen in Isopentane using standard procedures. Analysis of cryosections by fluorescent microscopy to quantify the FRET signal would provide additional information.

Example 11

This example describes a prophetic method for treating a genetic disease in mdx mice in an embodiment of the invention.

Eight mdx mice, which are used to model human muscular dystrophy, are treated with intramuscular injections of either native gentamicin or C-1 gentamicin. Four mice receive either gentamicin or the C-1 congener at a dose of about 1 mg/day and the other four mice receive the same compounds at a dose of about 5 mg/day. The animals are dosed over a period of 7 days. As controls, some normal mice and some mdx mice do not receive any gentamicin or C-1 but are otherwise treated the same as all of the other animals in the study. All mice are sacrificed, their skeletal muscle and their hearts are frozen and cryostat sectioned. The presence of dystrophin in these sections is investigated by immunohistochemistry.

Example 12

This example demonstrates a prophetic clinical trial of C-1 gentamicin in subjects with Duchenne muscular dystrophy in an embodiment of the invention.

In some patients with Duchenne muscular dystrophy (DMD), the disease is caused by a nonsense mutation (premature stop codon) in the gene that encodes the protein dystrophin. Gentamicin can partially restore dystrophin production in animals with muscular dystrophy due to the imposition of a premature stop codon in the gene encoding dystrophin (see, e.g., Example 7). The main purpose of this study is to understand whether the C-1 gentamicin can safely increase functional dystrophin protein in the muscles of patients with DMD due to a nonsense mutation.

Primary outcomes criteria for the study include: Dystrophin expression as assessed by immunofluorescence evaluation of tissue obtained by biopsy of the extensor digitorum brevis (EDB) muscle of the foot. Secondary Outcomes include: Presence of dystrophin mRNA and dystrophin-related proteins on EDB muscle biopsy, muscle function, compliance with treatment, safety, and PTC124 pharmacokinetics.

In this study, patients with DMD due to a mutation that introduces a premature stop codon in the gene encoding dystrophin are treated with C-1 gentamicin. To determine if a patient qualifies for the study, evaluation procedures are performed within 21 days prior to the start of treatment. The evaluation procedures include: obtaining the prospective participant's medical history; a physical examination; blood and urine tests to assess organ function; electrocardiogram (ECG); muscle biopsy for evaluation of dystrophin protein levels; and DMD-specific tests of muscle function. Eligible patients who elect to enroll in the study participate in a 28-day treatment period and a 28-day follow-up period (56 days total). The first 6 patients to enroll receive treatment with C-1 gentamicin at least once per day, each treatment comprises dosing each patient with about 5 mg/kg of C-1 gentamicin. These patients are monitored over a 28-day follow-up period without treatment. Subsequently, 18 additional patients are enrolled and receive treatment with C-1 gentamicin; these patients are treated at least once per day with a dose of about 10 mg/kg of C-1 gentamicin. These patients are monitored during a 28-day follow-up period without treatment.

To assess efficacy, patients will have an end-of-treatment biopsy and will undergo DMD-specific tests of muscle function. To assess safety and pharmacokinetics, safety assessments, blood and urine tests, and ECGs will be performed at pre-specified time points during the 28-day treatment period and the 28-day follow-up period. At the end of the 56 days, patients will be assessed periodically regarding their general health status; these evaluations will be performed by telephone contact at approximately 6-month intervals in the first 2 years and at approximately 12-month intervals in subsequent years (up to 5 years total).

All references, patents, patent applications and the like cited herein and not otherwise specifically incorporated by reference in their entirety, are hereby incorporated by reference in their entirety as if each were separately incorporated by reference in its entirety.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

An abstract is included to aid in searching the contents of the application and it is not intended to be read as explaining, summarizing or otherwise characterizing or limiting the invention in any way.

The present invention contemplates modifications as would occur to those skilled in the art. It is also contemplated that processes embodied in the present invention can be altered, duplicated, combined, or added to other processes as would occur to those skilled in the art without departing from the spirit of the present invention.

Further, any theory of operation, proof, or finding stated herein is meant to further enhance understanding of the present invention and is not intended to make the scope of the present invention dependent upon such theory, proof, or finding.

While the invention has been illustrated and described in detail in the figures, formulas and foregoing description, the description is considered to be illustrative and not restrictive in character. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. It is understood that only representative embodiments have been shown and described and that all changes and modifications that come within the spirit of the invention are considered part of the invention as though they were disclosed herein. Moreover, any combination of the above-described elements in all possible variations thereof is encompassed by the invention unless otherwise indicated herein or otherwise clearly contradicted by context.

The invention claimed is:

1. A method of treating a condition in a subject comprising administering a composition comprising C-1 gentamicin or a pharmaceutically acceptable acid addition salt thereof, wherein the composition is substantially free of C-1a gentamicin, C-2 gentamicin and C-2a gentamicin, and the condition is selected from the group consisting of a bacterial infection, a monogenic genetic disease and cancer.

2. The method of claim 1, wherein the condition is a monogenic genetic disease that is cystic fibrosis, Hurler Syndrome, Schele syndrome, Duchenne muscular dystrophy, Becker muscular dystrophy, nephrogenic diabetes insipidus, hemophilia, dystrophic epidermolysis bullosa, or Kabuki syndrome.

3. The method of claim 1, wherein the condition is cancer and wherein the cancer cells comprise a premature stop codon in a gene encoding a cell regulatory protein.

4. The method of claim 1, wherein the composition has a ratio of C-1a gentamicin to C-1 gentamicin of less than 1:10 (w/w).

5. The method of claim 1, wherein the composition has a ratio of C-2a gentamicin to C-1 gentamicin of less than 1:10 (w/w).

6. The method of claim 1, wherein the composition has a ratio of C-1 gentamicin to total gentamicin of greater than 9:10 (w/w).

7. The method of claim 1, wherein the composition is a liquid, and the composition comprises C-1 gentamicin at a concentration between about 1 mg/mL and about 115 mg/mL.

8. The method of claim 1, wherein the composition is a liquid, and the composition comprises less than 1000 ppm C-1a gentamicin.

9. The method of claim 1, wherein the composition is a liquid, and the composition comprises less than 1000 ppm C-2a gentamicin.

10. The method of claim 1, wherein the composition is a liquid, and the composition is for intravenous or intramuscular injection.

11. The method of claim 10, wherein the composition comprises greater than about 1 mg/kg total gentamicin.

12. The method of claim 1, wherein the composition further comprises at least one additional antibiotic.

13. The method of claim 1, wherein the composition comprises C-1 gentamicin or a pharmaceutically acceptable acid addition salt thereof in a therapeutically effective amount.

14. The method of claim 1, wherein the condition is a bacterial infection.

15. A composition comprising C-1 gentamicin or a pharmaceutically acceptable acid addition salt thereof, a preservative, and a chelating agent, wherein the composition is a liquid, and the composition is substantially free of C-1 a gentamicin, C-2 gentamicin and C-2a gentamicin.

16. The composition of claim 15, wherein the composition comprises less than 1000 ppm C-1a gentamicin.

17. The composition of claim 15, wherein the composition comprises less than 1000 ppm C-2a gentamicin.

* * * * *